(12) United States Patent
Wang et al.

(10) Patent No.: US 11,980,462 B2
(45) Date of Patent: *May 14, 2024

(54) SALIVARY BIOSENSORS AND BIOFUEL CELLS

(71) Applicant: THE REGENTS OF THE UNIVERSITY OF CALIFORNIA, Oakland, CA (US)

(72) Inventors: Joseph Wang, San Diego, CA (US); Patrick Mercier, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 851 days.

This patent is subject to a terminal disclaimer.

(21) Appl. No.: 16/789,316

(22) Filed: Feb. 12, 2020

(65) Prior Publication Data

US 2020/0367793 A1 Nov. 26, 2020

Related U.S. Application Data

(63) Continuation of application No. 15/112,816, filed as application No. PCT/US2015/012309 on Jan. 21, 2015, now Pat. No. 10,595,759.

(Continued)

(51) Int. Cl.
*A61B 5/1486* (2006.01)
*A61B 5/00* (2006.01)
(Continued)

(52) U.S. Cl.
CPC ........ *A61B 5/1486* (2013.01); *A61B 5/14507* (2013.01); *A61B 5/6802* (2013.01);
(Continued)

(58) Field of Classification Search
None
See application file for complete search history.

(56) References Cited

U.S. PATENT DOCUMENTS 5,720,862 A 2/1998 Hamamoto et al.
9,502,730 B2 11/2016 Wang et al.
(Continued)

FOREIGN PATENT DOCUMENTS

CN 1139757 A 1/1997
EP 2682745 A1 1/2014
(Continued)

OTHER PUBLICATIONS

INPI, Search Report received for Brazilian Patent Application No. BR112016016761-9. Dated Jun. 8, 2020. 4 pages with English translation.

(Continued)

*Primary Examiner* — Michael R Bloch
(74) *Attorney, Agent, or Firm* — Perkins Coie LLP

(57) ABSTRACT

Methods, systems, and devices are disclosed mouth-based biosensors and biofuel cells. In one aspect, an electrochemical sensor device for detecting analytes in saliva includes a substrate including an electrically insulative material, a first electrode disposed on the substrate at a first location, in which the first electrode includes a surface including a chemical agent (e.g., a catalyst or a reactant) corresponding to an analyte in saliva; and a second electrode disposed on the substrate at a second location separated from the first electrode by a spacing region, the first and second electrodes capable of sustaining a redox reaction involving the chemical agent and the analyte to produce an electrical signal, such that, when the device is present in the mouth of a user and electrically coupled to an electrical circuit, the device is operable to detect the analyte in the user's saliva.

20 Claims, 16 Drawing Sheets

Related U.S. Application Data

(60) Provisional application No. 61/929,946, filed on Jan. 21, 2014.

(51) Int. Cl.

| | | |
|---|---|---|
| *A61B 5/145* | (2006.01) | |
| *A61C 19/04* | (2006.01) | |
| *H01M 8/0239* | (2016.01) | |
| *H01M 8/16* | (2006.01) | |
| *H01M 8/22* | (2006.01) | |
| *A61B 10/00* | (2006.01) | |
| *G01N 27/327* | (2006.01) | |

(52) U.S. Cl.
CPC .............. *A61B 5/682* (2013.01); *A61C 19/04* (2013.01); *H01M 8/0239* (2013.01); *H01M 8/16* (2013.01); *H01M 8/22* (2013.01); *A61B 5/14532* (2013.01); *A61B 5/14546* (2013.01); *A61B 5/7225* (2013.01); *A61B 10/0051* (2013.01); *A61B 2560/0214* (2013.01); *A61B 2560/0462* (2013.01); *A61B 2562/0295* (2013.01); *G01N 27/3272* (2013.01); *Y02E 60/50* (2013.01)

(56) References Cited

U.S. PATENT DOCUMENTS

| | | | | |
|---|---|---|---|---|
| 2004/0045821 | A1* | 3/2004 | Cui | C12Q 1/004 204/403.02 |
| 2004/0245101 | A1* | 12/2004 | Willner | H01M 8/16 204/403.01 |
| 2005/0113654 | A1 | 5/2005 | Weber et al. | |
| 2007/0032717 | A1 | 2/2007 | Brister et al. | |
| 2007/0048181 | A1 | 3/2007 | Chang et al. | |
| 2007/0106138 | A1* | 5/2007 | Beiski | A61B 5/682 600/549 |
| 2007/0197890 | A1 | 8/2007 | Boock et al. | |
| 2008/0118782 | A1* | 5/2008 | Heller | C12Q 1/26 429/432 |
| 2008/0176271 | A1 | 7/2008 | Silver et al. | |
| 2009/0101498 | A1 | 4/2009 | Papadimitrakopoulos et al. | |
| 2011/0117453 | A1* | 5/2011 | Tokita | H01M 8/16 429/401 |
| 2011/0184319 | A1 | 7/2011 | Mack et al. | |
| 2011/0250510 | A1* | 10/2011 | Cinquin | C12N 9/0006 429/535 |
| 2011/0319734 | A1 | 12/2011 | Gottlieb et al. | |
| 2012/0172677 | A1* | 7/2012 | Logan | A61B 5/083 600/301 |
| 2013/0053666 | A1 | 2/2013 | Hughes et al. | |
| 2013/0066236 | A1* | 3/2013 | Herman | A63B 71/085 600/595 |
| 2014/0012114 | A1* | 1/2014 | Zevenbergen | A61B 5/14517 600/346 |

FOREIGN PATENT DOCUMENTS

| | | |
|---|---|---|
| WO | 2011091347 A2 | 7/2011 |
| WO | 2011117357 A2 | 9/2011 |
| WO | 2013039455 A1 | 3/2013 |
| WO | 2013130145 A2 | 9/2013 |

OTHER PUBLICATIONS

Aguirre et al., "Sialochemistry: A Diagnostic Tool?", Crit. Rev. Oral Biol. Med., 1993, 4, pp. 343-350.
Altagracia-Martinez et al., "Prussian blue as an antidote for radioactive thallium and cesium poisoning", Orphan Drugs: Research and Reviews, 2012, 2, pp. 13-21.
Claver et al., "Disposable electrochemiluminescent biosensor for lactate determination in saliva", Analyst, 2009, 134, pp. 1423-1432.
Benedet et al., "Amperometric sensing of hydrogen peroxide vapor for securing screening", Anal. Bioanal. Chem., 2009, 395, pp. 371-376.
Bonato, "Wearable Sensors and Systems: From Enabling Technology to Clinical Applications", IEEE Eng. Med. Biol. Mag., 2010, 29.3, pp. 25-36.
Chicharro et al., "Saliva Composition and Exercise", Sports Med., 1998, 26, pp. 17-27.
CNIPA, Office Action for Chinese Patent Application No. 201580013394.7, dated Mar. 30, 2018, 5 pages.
CNIPA, Office Action for Chinese Patent Application No. 201580013394.7, dated Oct. 26, 2018, 15 pages.
Dawes, "The effects of flow rate and duration of stimulation on the concentrations of protein and the main electrolytes in human parotid saliva", Arch. Oral Biol., 1969, 14, pp. 277-294.
Dempsey et al., "Electropolymerised 0-phenylenediamine film as means of immobilising lactate oxidase for L-lactate biosensor", Talanta, 1993, 40, pp. 445-451.
Diamond et al., "Wireless Sensor Networks and Chemo-/Biosensing", Chem. Rev., 2008, 108, pp. 652-679.
Dong et al., "The effects of chewing frequency and duration of gum chewing on salivary flow rate and sucrose concentration", Arch. Oral Biol., 1995, 40, pp. 699-705.
EPO, Extended European Search Report for European Patent Application No. 15740704.0, dated Jul. 19, 2017, 9 pages.
EPO, Official Action for European Patent Application No. 15740704.0, dated Apr. 12, 2018, 8 pages.
Esashi et al., "Integrated Micro Multi Ion Sensor Using Field Effect of Semiconductor", IEEE Trans. Biomed. Eng., 1978, 2, pp. 184-192.
Graf et al., "Oral Telemetry of Fluoride Ion Activity", Arch. Oral Biol., 1969, 14, pp. 259-263.
Graf et al., "Telemetry of Plaque pH from Interdental Area", Helv. Odontol. Acta, 1966, 10, pp. 94-101.
Hoffman, "Thallium Toxicity and the Role of Prussian Blue in Therapy", Toxicol. Rev., 2003, 22, pp. 29-40.
Humphrey et al., "A review of saliva: Normal composition, flow, and function", J. Prosthet. Dent., 2001, 85, pp. 162-169.
ISA, International Search Report and Written Opinion of PCT/US2015/012309 mailed by the ISA/US dated Apr. 17, 2015 (10 pages).
Jia et al., "Electrochemical Tattoo Biosensors for Real-Time Noninvasive Lactate Monitoring in Human Perspiration", Anal. Chem. 2013, 85, pp. 6553-6560.
JPO, Office Action for Japanese Patent Application No. 2016-565134, dated Nov. 6, 2018, 3 pages.
Kagie et al., "Flexible Rolled Thick-Film Miniaturized Flow-Cell for Minimally Invasive Amperometric Sensing", Electroanalysis, 2008, 20, pp. 1610-1614.
Kim et al., "Non-invasive mouthguard biosensor for continuous salivary monitoring of metabolites," Analyst. Apr. 7, 2014;139(7):1632-6.
Lowry, "Characterization of Glucose Oxidase-Modified Poly(phenylenediamine)-Coated Electrodes in Vitro and in Vivo: Homogeneous Interference by Ascorbis Acid in Hydrogen Peroxide Detection", Anal. Chem., 1994, 66, 1754-1761.
Makila et al., "A study of ascorbic acid in human saliva", Arch. Oral Biol., 1969, 14, pp. 1285-1292.
Mannoor et al., "Graphene-based wireless bacteria detection on tooth enamel", Nat. Comm., 2012, 3, 9 pages.
Minamitani et al., "a Denture Base Type of Sensor System for Simultaneous Monitoring of Hydrogen Ion Concentration pH and Tissue Temperature in the Oral Cavity", IEICE Trans. Inf. & Sys., 2002, 85, pp. 22-29.
Navazesh, "Methods for Collecting Saliva", Ann N.Y. Acad. Sci., 1993, 694, pp. 72-77.
Newsome et al., "The role of the mouthguard in the prevention of sports-related dental injuries: a review" Int. J. Paediatr. Dent., 2001, 11, pp. 396-404.

(56) References Cited

OTHER PUBLICATIONS

O'Halloran et al., "Prussian Blue bulk modified screen-printed electrodes for H2)2 detection and for biosensors", Talanta, 2001, 55, pp. 605-611.
Ricci et al., "Sensor and biosensor preparation, optimisation and applications of Prussian Blue modified electrodes", Biosens. Bioelectron., 2005, 21, pp. 389-407.
Santos et al., "effects of 3-km race upon salivary lactate correlation with blood lactate", Com. Biochem. Physiol., Part B: Biochem. Mol. Biol., 2006, 145, pp. 114-117.
Schabmueller et al., "Micromachined sensor for lactate monitoring in saliva", Biosens. Bioelectron., 2006, 21, pp. 1770-1776.
Segura et al., "A new approach to the assessment of anaerobic metabolism: measurement of lactate in saliva", Br. J. Sports Med., 1996, 30, pp. 305-309.
Soukup et al., "Salivary uric acid as a noninvasive biomarker of metabolic syndrome", Diabetol. Metab. Syndr., 2012, 4, 5 pages.
Tekus et al., "Comparison of blood and saliva lactate level after maximum intensity exercise", Acta Biol. Hung., 2012, 63, pp. 89-98.
Thomas et al., "A contact lens with an integrated lactate sensor", Sens. Actuators, B, 2012, 162, pp. 128-134.
Windmiller et al., "Bicomponent Microneedle Array Biosensor for Minimally-Invasive Glutamate Monitoring", Electroanalysis, 2011, 23, pp. 2302-2309.
Windmiller et al., "Wearable Electrochemical Sensors and Biosensors: A Review", Electroanalysis, 2013, 25, pp. 29-46.
Yang et al., "Quantitative measurement of cyanide released from Prussian Blue", Clin. Toxicol., 2007, 45, pp. 776-781.
Zagatto et al., "Comparison between the use of saliva and blood for the minimum lactate determination in arm ergometer and cycle ergometer in table tennis players", Rev. Bras. Med. Esporte, 2004, 10, pp. 475-480.
IPI, Examination Report for Indian Patent Application No. 201617024183. Mail Date: Mar. 18, 2021. 11 pages.

\* cited by examiner

SALIVARY BIOSENSORS AND BIOFUEL CELLS

CROSS REFERENCE TO RELATED APPLICATIONS

This patent document is a continuation of U.S. patent application Ser. No. 15/112,816, entitled "SALIVARY BIOSENSORS AND BIOFUEL CELLS" filed on Jul. 20, 2016, which is a U.S.C. § 371 National Stage application of International Application No. PCT/US2015/012309, entitled "SALIVARY BIOSENSORS AND BIOFUEL CELLS" filed on Jan. 21, 2015 which further claims benefit of priority of U.S. Provisional Patent Application No. 61/929,946, entitled "MOUTH-BASED BIOSENSORS AND BIOFUEL CELLS", filed on Jan. 21, 2014. The entire contents of the aforementioned patent applications are incorporated by reference as part of the disclosure of this application.

STATEMENT REGARDING FEDERALLY SPONSORED RESEARCH OR DEVELOPMENT

This invention was made with government support under grant CBET-1066531 awarded by the National Science Foundation (NSF). The government has certain rights in the invention.

TECHNICAL FIELD

This patent document relates to molecular sensor technologies for sensing biological substances, chemical substances and other substances and fuel cell technologies.

BACKGROUND

Sensors based on electrochemical processes can be used to detect a chemical substance or a biological substance (e.g., an organism) by using a transducing element to convert a detection event into a signal for processing and/or display. Biosensors can use biological materials as the biologically sensitive component, e.g., such as biomolecules including enzymes, antibodies, nucleic acids, etc., as well as living cells. For example, molecular biosensors can be configured to use specific chemical properties or molecular recognition mechanisms to identify target agents. Biosensors can use the transducer element to transform a signal resulting from the detection of an analyte by the biologically sensitive component into a different signal that can be addressed by optical, electronic or other means. For example, the transduction mechanisms can include physicochemical, electrochemical, optical, piezoelectric, as well as other transduction means.

A fuel cell is a device that converts chemical energy from a substance (e.g., referred to as a fuel) into electrical energy (e.g., electricity). Generally, the energy conversion includes a chemical reaction with oxygen or another oxidizing agent. For example, hydrogen is among a common fuel, and hydrocarbons such as natural gas and alcohols can also be used in fuel cells. For example, fuel cells differ from batteries in that they require a constant source of fuel and oxygen to operate, but can produce electricity continually provided the fuel and oxygen inputs are supplied to the fuel cell.

SUMMARY

Disclosed are mouth-based devices and systems that function as biosensors and biofuel cells (BFC). In some implementations, wearable saliva metabolite biosensor devices include printable enzyme electrodes integrated into a mouthguard that exhibit high sensitivity, selectivity and stability using whole human saliva samples for providing non-invasive and real-time information regarding the wearer's health, performance, and stress level. In some implementations, the wearable mouth-worn biofuel cell devices include structures formed on the surface of a mouthguard to harvest power from saliva. Applications of the disclosed devices and systems include biomedical and fitness monitoring and wearable BFCs for powering various wearable/portable devices.

In one aspect, an electrochemical sensor device for detecting analytes in saliva includes a substrate including an electrically insulative material; a first electrode disposed on the substrate at a first location, in which the first electrode includes a surface including a chemical substance that includes a catalyst or a reactant corresponding to an analyte in saliva; and a second electrode disposed on the substrate at a second location separated from the first electrode by a spacing region, the first and second electrodes capable of sustaining a redox reaction including the chemical substance and analyte to produce an electrical signal, such that, when the device is present in the mouth of a user and electrically coupled to an electrical circuit, the device is operable to detect the analyte in the user's saliva.

In one aspect, a method to detect an analyte in saliva and power a device from the saliva includes extracting electrical energy, at anode and cathode electrodes of a biofuel cell attached to a mouth-based device wearable in the mouth of a user, from a biofuel substance present in saliva by converting the biofuel substance to a first product in an oxidative process that releases electrons captured at the anode and reducing a chemical substance in the saliva to a second product in a chemical reduction process in which the second product gains electrons at the cathode; supplying the extracted electrical energy to electrodes of an electrochemical sensor attached to the mouth-based device to activate the electrochemical sensor; and detecting, at the electrodes of the activated electrochemical sensor in contact with saliva in the user's mouth, an electrical signal produced as a result of a redox reaction involving an analyte in the saliva and a chemical agent coupled to an electrode of the electrochemical sensor.

In one aspect, a device to detect an analyte in saliva and power a device from the saliva includes a substrate including an electrically insulative material, in which the substrate is structured to attach to a mouth-worn device that can fit inside a user's mouth; an electrochemical sensor to detect a salivary analyte; a biofuel cell to electrochemically extract energy from the saliva to provide electrical power to the device, and an electrical circuit electrically coupled between the biofuel cell and the electrochemical sensor via electrical interconnects to obtain the extracted energy as electrical energy from the biofuel cell and to supply the electrical energy to the electrochemical sensor. The electrochemical sensor includes a first electrode disposed on the substrate at a first location, in which the first electrode includes a surface including a chemical substance including a catalyst or a reactant corresponding to the salivary analyte; and a second electrode disposed on the substrate at a second location separated from the first electrode by a spacing, in which the first and second electrodes are operable to sustain a redox reaction involving the chemical substance and the salivary analyte to produce an electrical signal detectable by the first and second electrodes. The biofuel cell includes an anode disposed on the substrate and including an electrically conductive material, the anode including a fuel cell catalyst to facilitate the conversion of a fuel substance in the saliva to a first product in an oxidative process that releases electrons captured at the anode, thereby extracting energy from the fuel substance, and a cathode disposed on the substrate adjacent to and separated from the anode, the cathode including a material that is electrically conductive and capable of reducing an oxygenated substance in the saliva to a second product in a chemical reduction process in which the second product gains electrons. When the device is present in the mouth of the user, the device is operable to detect the salivary analyte in the user's saliva.

The subject matter described in this patent document can be implemented in specific ways that provide one or more of the following features. For example, the disclosed systems and devices are capable of real-time monitoring of metabolites and electroactive constituents of saliva and can offer continuous energy harvesting for powering of in-mouth electronics.

DETAILED DESCRIPTION

Figure 1A:
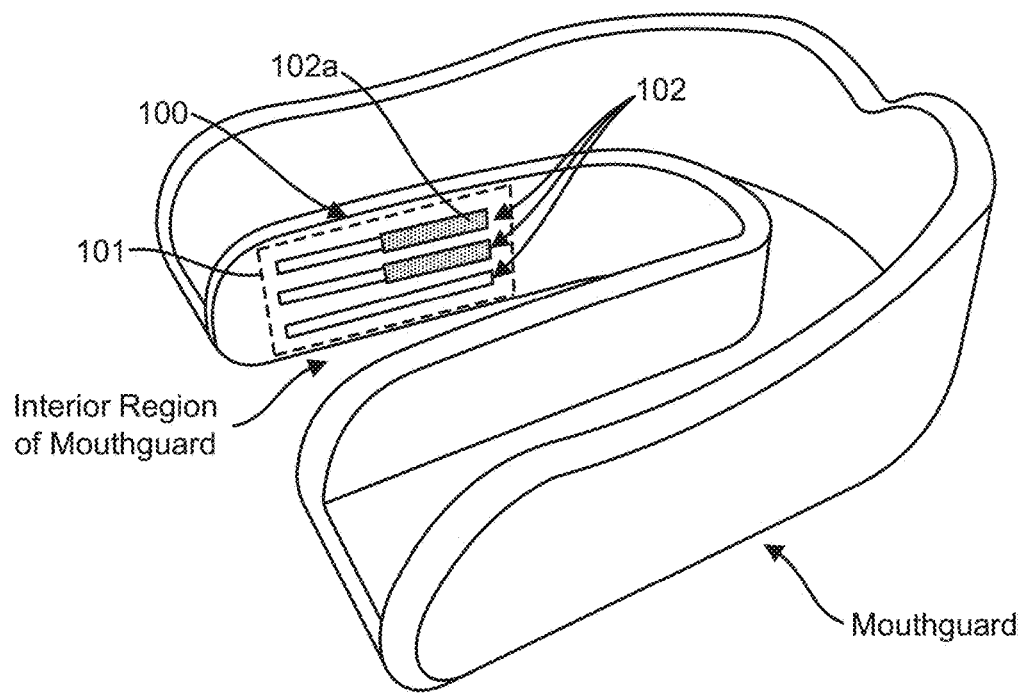
FIG. 1A shows a schematic illustration of an exemplary salivary electrochemical sensor device of the disclosed technology employed in a mouthguard.

Wearable biosensors have been gaining considerable interest owing to their promise for real-time monitoring of the wearer's health and fitness in a wide range of biomedical, sport and military scenarios. Earlier work on wearable biosensor devices and systems has typically focused on monitoring vital signs from physical signals, such as electrocardiography and pulse oximetry. Yet, non-invasive wearable electrochemical sensors can yield useful insights into the overall health status and performance of individuals beyond physical parameters alone.

Wearable biosensors can be used for detecting chemical biomarkers in human fluids that can be obtained non-invasively, e.g., tears, sweat or saliva. Of these exemplary fluids, saliva can be extremely attractive for such non-invasive monitoring, in part due to its continuous and convenient availability. Additionally, saliva has good correlation with blood concentrations of numerous analytes. Such correlation reflects the permeation of multiple constituents from blood to saliva via transcellular or paracellular paths. For example, sialochemistry can be a useful non-invasive alternative to blood analysis for monitoring the hormonal, stress and metabolic states of individuals. Existing salivary sensor systems such as denture-based pH and temperature sensors or bacteria cytosensors are indwelling units that are not capable of being used as non-invasive wearable biosensors for monitoring salivary metabolites, e.g., despite the established high correlation between the level of salivary metabolites and their corresponding blood concentration.

Furthermore, mouthguard-like devices represent an example for the challenge of 3D integration of sensing and electronics within a wearable device. Such devices offer a unique potential to sense in real-time biomarkers in saliva with the ability to yield complex and continuous information about the well-being of the wearer. Presently, there are impact monitoring mouthguards in the market. These impact monitoring mouthguard devices, however, focus mainly on impact-related injury in sports and do not involve chemical sensing or power harvesting.

Disclosed are wearable electrochemical sensor and energy generation techniques, systems, and devices that detect and utilize metabolites in saliva of a user's mouth.

The wearable biosensor and biofuel cells (BFC) devices of the disclosed technology can include printable enzyme electrodes integrated into a mouthguard that exhibit high sensitivity, selectivity and stability using whole human saliva samples for providing non-invasive and real-time information regarding the wearer's health, performance, and stress level. The disclosed mouth-worn biosensor and BFC devices can include structures formed on the surface of a mouthguard to harvest power from saliva. Applications of the disclosed devices and systems include biomedical and fitness monitoring and wearable BFCs for powering various wearable/portable devices.

In one aspect, the disclosed technology includes non-invasive electrochemical biosensors, which can be employed in a mouthguard or other wearable item in the mouth of a user, to provide continuous monitoring of salivary metabolites. Exemplary embodiments of the disclosed electrochemical sensor devices are described in this patent document, and exemplary implementations were performed that demonstrate the in-mouth biosensor concept, including an exemplary printable amperometric enzymatic biosensor integrated onto an easily-removable mouthguard platform for non-invasive monitoring of salivary analytes, e.g., including lactate. For example, the exemplary electrochemical sensor devices can employ one or more types of enzymes on the electrodes that are selected to interact with target analytes (e.g., the corresponding enzymatic substrate) in the saliva. The mouthguard employing the disclosed electrochemical biosensor devices can include a saliva-based biofuel cell device to extract energy from chemical constituents in the saliva, which can be used to power the electrochemical biosensor devices and electrical circuits and/or electronic devices incorporated in the mouthguard.

Mouthguards are widely used by athletes in competitive and recreational sports as they offer considerable protection against sports-related dental injuries. Mouthguards are typically polymeric articles designed fit firmly and snuggly over the teeth, and represent an attractive platform with sufficient volume for mounting miniaturized sensors, control/acquisition electronics and wireless transmitters. Unlike earlier reported permanent indwelling saliva sensors, the disclosed technology includes electrochemical sensor devices employed in a mouthguard that can be easily worn and replaced without any specialized assistance. Importantly, since the exemplary wearable sensor and actuator device is configured to always be in direct contact with saliva, physiological information can be measured in real-time without interruption, thereby opening a new avenue for continuous assessment of dynamic metabolites changes.

Exemplary device and system designs and operational techniques of mouthguard-based amperometric biosensors and biofuel cells of the present technology using metabolites, electroactive species and biofuels naturally present in saliva are described.

Figure 1B:
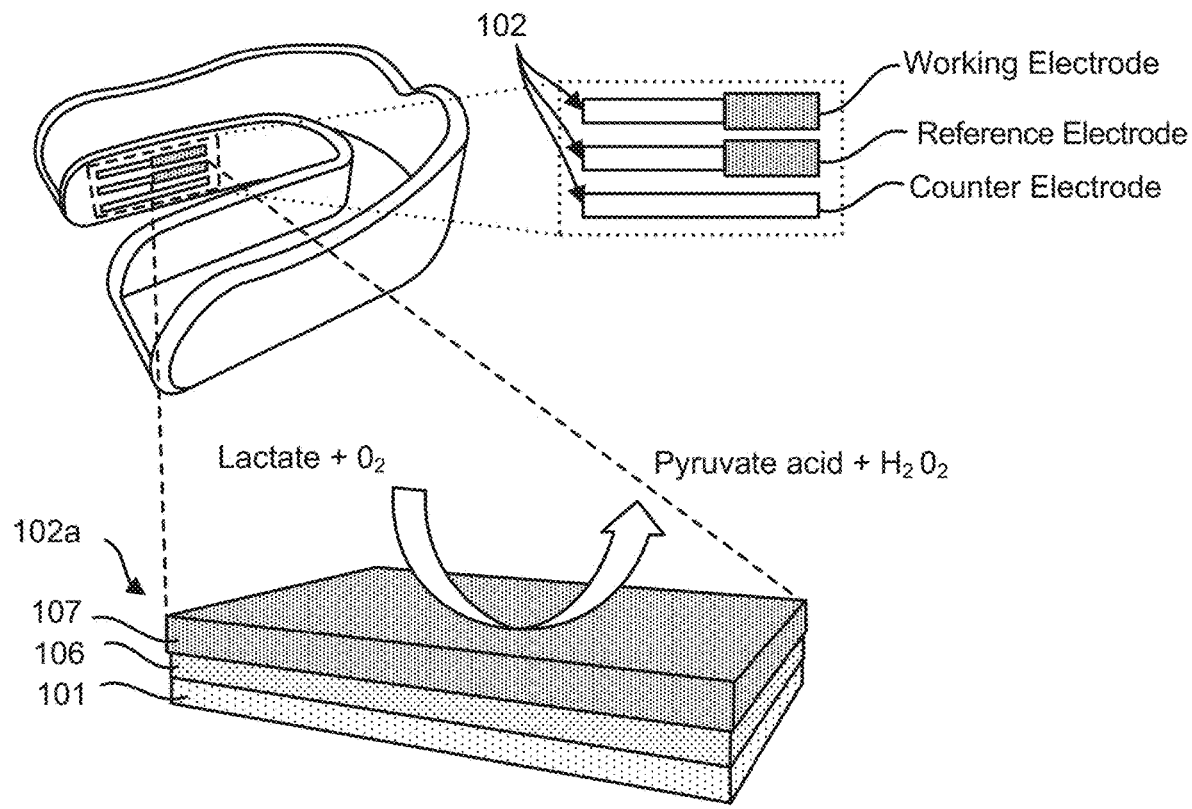
FIG. 1B shows a schematic illustration of an exemplary electrode configuration of the device in FIG. 1A designed for salivary lactate monitoring.

FIG. 1A shows a schematic illustration of a salivary electrochemical sensor device 100 of the disclosed technology employed in a mouthguard that can be worn in a user's mouth. The electrochemical sensor 100 includes a substrate 101 including an electrically insulative material. The electrochemical sensor 100 includes an electrode contingent 102 including two or more electrodes disposed on the substrate 101. For example, the electrodes of the electrode contingent 102 can include an electrically conductive material, which can include an electrocatalytic material. In one embodiment, the electrode contingent 102 includes a working electrode and a counter electrode. The working electrode is disposed on the substrate 101, and the counter electrode disposed on the substrate 101 at a location separated from the working electrode (e.g., by a spacing). The working electrode is configured in an electrode structure 102a, as shown in FIG. 1B. The electrode structure 102a includes an electrically conductive material 106 disposed on the substrate 101, in which the electrically conductive material 106 is coated by an electrochemical transducer layer 107 including a chemical substance to cause a electrochemical reaction that is detectable at the electrodes of the electrode contingent 102. For example, in some implementations, the chemical substance includes a catalyst to selectively catalyze a corresponding analyte in the saliva to cause or facilitate a reaction that produces a detectable signal at the electrodes 102. In some implementations, for example, the chemical substance contained in the layer 107 includes a chemical reactant to chemically react with the corresponding analyte in the saliva to create the detectable signal at the electrodes 102. The electrodes 102 are capable of sustaining a redox reaction to produce an electrically charged species that can be transduced as an electrical signal at the electrodes, such that, when the electrochemical sensor device 100 is present in the mouth of a user and electrically coupled to an electrical circuit, the sensor device 100 is operable to detect the chemical analyte in the user's saliva of the mouth. In the example shown in FIG. 1B, the chemical substance contained in the electrochemical transducer layer 107 includes lactate oxidase (LOx), which can catalyze a redox reaction with lactate (e.g., the selected analyte in the saliva to be detected) that generates the electrical signal at the electrodes 102.

In the exemplary embodiment of the salivary biosensor device 100 shown in FIGS. 1A and 1B, the electrode contingent 102 includes three electrodes: a working electrode including the electrode structure 102a, the counter electrode, and a reference electrode including the electrode structure 102a positioned between the working and counter electrodes. In some embodiments, for example, the electrochemical sensor device 100 can include an array of the electrode contingents 102, e.g., such as an array of working electrodes, counter electrodes, and/or reference electrodes.

In some aspects, the disclosed salivary biosensor device 100 can be integrated with a salivary biofuel cell and an electrical circuit (e.g., including data processing and communication electronics) on the mouthguard or other mouth-based platform, which generates electrical power to deliver to the electrical circuit and the biosensor device such that the integrated device can provide autonomous and continuous monitoring of substances in a user's saliva. Biofuel cells are a class of fuel cell devices that employ enzymes or microbes as a bioprocessing contingent to derive power from various fuel substances such as organic, biochemical, and/or biological compounds which can be found in a variety of biological mediums. Biofuel cells of the present technology can provide a safe and sustainable energy supply source to power the salivary biosensor and electronics, while only minimally increasing the footprint of the overall device platform employed on the mouthguard or other mouth-worn device. Biofuel cells of the present technology include biocompatible materials for safely converting chemical energy from the environment to which they are employed into electrical energy supplied to sensor devices that continuously monitor the same environment. The disclosed biofuel cells can be advantageous over batteries or other field-deployable power supplies because they provide higher energy density (e.g., in the case of both batteries and photovoltaics), longer operational lifetime, and lighter weight (e.g., in the case of batteries). For example, by employing the disclosed biofuel cell devices for powering the salivary sensor and electronics in the mouth-based device, dangerous risks associated with chemical leeching from battery units are eliminated. The disclosed technology includes biofuel cell devices capable of direct electron transfer from selected biocatalysts in saliva, which the biofuel cell devices integrate with the biosensor devices in a mouth-based platform.

Figure 1C:
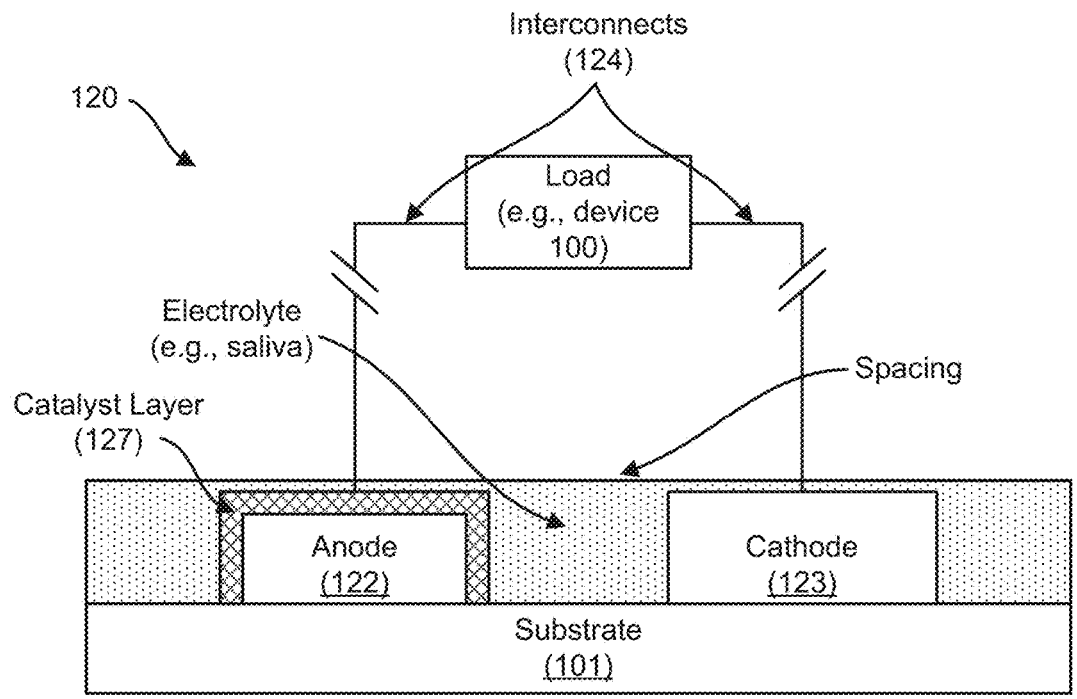
FIG. 1C shows a block diagram of an exemplary embodiment of a biofuel cell device of the present technology.

FIG. 1C shows a block diagram of an exemplary embodiment of a biofuel cell device 120 of the present technology. The biofuel cell device 120 includes an anode electrode 122 and a cathode electrode 123 on a substrate (e.g., the substrate 101 of the electrochemical sensor device 100), in which the anode electrode 122 and the cathode electrode 123 are positioned adjacent to and separated from one another by a spacing region. The anode electrode 122 includes a catalyst layer 127 containing a catalyst to a biofuel substance (e.g., found in saliva), in which the catalyst layer 127 can be configured to the anode 122 in at least one of the following configurations: (1) the catalyst layer 127 is integrated within the anode electrode 122, i.e., the catalyst is dispersed within the anode material of the anode electrode 122; (2) the catalyst is coated on the surface of the anode electrode 122 to form the catalyst layer 127, which can be electrostatically anchored or covalently bonded to the surface of the anode electrode 122; and (3) the catalyst layer 127 is structured to include an electropolymerized conducting polymer formed on the surface of the anode electrode 122 to entrap the catalyst within the polymer film, and/or the catalyst layer 127 is structured to include a selectively permeable scaffold structure, e.g., such as Nafion or chitosan, formed on the surface of the anode electrode 122 to entrap the catalyst within the scaffold. The biofuel device 120 includes individual interconnects 124 that are electrically coupled to the anode and the cathode electrodes 122 and 123, respectively, to electrically connect the anodic and cathodic electrodes to the load to which the extracted energy is supplied, e.g., the electrochemical sensor device 100.

In operation, the electrolytic saliva fluid containing the fuel substance makes contact with the surface of the biofuel cell 120 such that the saliva can immerse the spacing between the anode electrode 122 and cathode electrode 123. The catalyst is selected to facilitate the conversion of a corresponding fuel substance (e.g., biofuel constituent) in the saliva to a first product in an oxidative process that releases electrons captured at the anode, thereby extracting energy from the fuel substance, in which the cathode is capable of reducing an oxygenated substance in the biological fluid to a second product in a chemical reduction process in which the second product gains electrons, in which the biofuel cell device 120 obtains the extracted energy as electrical energy. The electrolytic fluid can include various biofuel constituents, e.g., such as glucose, lactic acid, uric acid, or other. For example, the catalyst contained in the catalyst layer 127 can include LOx, GOx, or uricase, or other catalyst (e.g., oxidase or dehydrogenase) corresponding to a biofuel substance in saliva. In some embodiments of the biofuel cell device 120, the biofuel cell device can include a proton-exchange membrane separator attached to the substrate 101 employed in the spacing region to inhibit the conduction of electrons through the electrolytic medium.

Figure 1D:
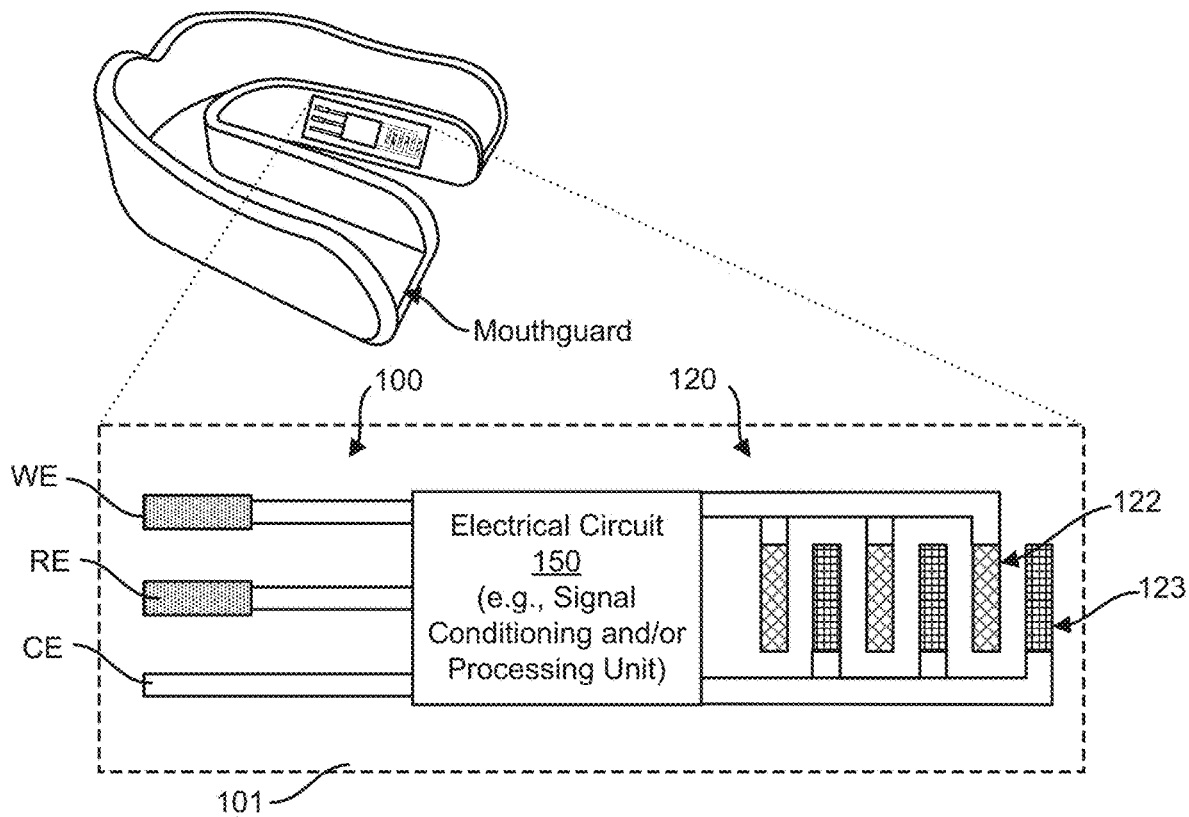
FIG. 1D shows a schematic illustration of an integrated salivary biosensor and fuel cell device of the disclosed technology employed in a mouthguard.

FIG. 1D shows a schematic illustration of an integrated salivary biosensor and fuel cell device of the disclosed technology employed in a mouthguard that can be worn in a user's mouth. The integrated sensor-fuel cell device can include the electrochemical sensor device 100 (e.g., in either two- or three-electrode configuration) and the biofuel cell device 120 electrically interfaced to an electrical circuit 150. The circuit 150 can include electrical circuit elements (e.g., impedance elements, diodes, transistors, etc.) and/or electronic components (e.g., processors, A/D converters, wireless transmitter/receiver, instrumentation electronics, etc.) to provide signal conditioning, signal and data processing, storage, and/or communication. For example, the circuit 150 can be configured to control the electrochemical analysis techniques to detect the salivary analyte or analytes of interest by the sensor 100, e.g., including but not limited to chronoamperometry, chronopotentiometry, voltammetry, cyclic voltammetry, linear sweep electrochemical techniques, polarography, pulsed electrochemical analysis techniques, impedance spectroscopy, etc.

In the example shown in FIG. 1D, the exemplary biofuel cell device 120 includes an interdigitated array of the anode and cathode electrodes 122 and 123 configured on the substrate 101. The array of anode and cathode electrodes 122 and 123 are connected to the conduits 124 that electrically connect to the circuit 150. In some implementations of the biofuel cell device 120, the biofuel cell array can further include an electrically conductive underlayer, e.g., formed of an electrically conductive material such as silver or copper, on the substrate 101 and underneath the interdigitated array of the anode and cathode electrodes 122 and 123 and conduits 124. In some implementations, the biofuel cell device 120 can further include a reservoir region on the substrate 101 structured to contain the biological fluid in a region surrounding the interdigitated array of the anode and cathode electrodes 122 and 123.

Exemplary Lactate Biosensors

In one embodiment, a non-invasive mouthguard-based biosensor device is described for continuous salivary monitoring of the salivary metabolite lactic acid (or lactate) using amperometric monitoring. For example, salivary lactate concentrations correspond well with blood lactate levels and have been used in vitro for monitoring fitness levels. Saliva may therefore be suited as a fluid for continuous non-invasive monitoring of lactate levels during sport activities. The exemplary wearable oral biosensory system described here includes a printable Prussian-Blue (PB) transducer and a poly-orthophenylenediamine (PPD)/lactate-oxidase (LOx) reagent layer. For example, the Prussian-Blue transducer can act as "artificial peroxidase", which offers a highly selective detection of the hydrogen peroxide product of oxidase biocatalytic reactions. PB can be used for oral treatment of poisoning by heavy metals, e.g., such as thallium and cesium, and its use appears to be very safe under physiological conditions even following high oral doses. Poly-orthophenylenediamine (PPD) is employed for the electropolymeric entrapment of oxidases, rejection of potential interferences, and protection of the biosensor surface. The coupling of the extremely low-potential detection of the peroxide product afforded by the PB transducer and the exclusion of electroactive constituents of whole saliva leads to high selectivity and stability. An embodiment of the exemplary salivary lactate sensor device can include the electrochemical sensor device 100 shown in FIGS. 1A and 1B.

The following describes exemplary designs and in vitro characterizations of the exemplary mouthguard-based biosensor used in implementations of continuous in-mouth monitoring of lactate. The exemplary mouthguard enzymatic biosensor, which includes printable enzyme electrode including immobilized lactate oxidase, can detect low potentials of the peroxide product and exhibits high sensitivity, selectivity and stability using whole human saliva samples. The exemplary device can be used to tender useful real-time information regarding a wearer's health, performance and stress level, and thus hold considerable promise for diverse biomedical and fitness applications. Other biochemicals present in saliva can also be used in other exemplary implementations of the disclosed biosensor devices.

Exemplary implementations of the exemplary mouthguard lactate biosensor included the following chemicals and reagents. L-Lactate oxidase (LOx) (activity: 101 U/mg) was obtained. 1,2-Phenylenediamine (o-Pd), L-lactic acid, L-ascorbic acid (AA), uric acid (UA), sodium sulfate, potassium phosphate monobasic, potassium phosphate dibasic, and sodium chloride were obtained and were used without further purification or modification. Ultrapure water (18.2 MΩ·cm) was employed in the exemplary implementations.

The exemplary implementations of the exemplary mouthguard lactate biosensor included the following instrumentation. A CH Instruments model 440 analyzer was employed for the electrochemical measurements. Chronoamperometric studies were carried out to evaluate the response of mouthguard sensors. For example, the applied potentials in the exemplary implementations were versus the printed screen-printed pseudo Ag/AgCl reference electrode at room temperature (e.g., 22° C.). A MPM SPM semi-automatic screen printer was used for printing electrodes. The exemplary sensor patterns were designed using AutoCAD, and stencils were patterned on 75 μm-thick stainless steel stencils.

The exemplary mouth-based electrochemical sensor device shown in FIGS. 1A and 1B can be fabricated using the following fabrication techniques, and integrated into a mouthguard. In one example, the mouthguard biosensors were fabricated by screen-printing three separate layers on a flexible PET substrate, e.g., polyethylene terephthalate. In the first layer, an Ag/AgCl conductive ink (e.g., 124-36, medical grade, from Creative Materials Inc., MA USA) was printed first to provide the reference electrode as well as the contacts for interfacing the three electrodes to the electrochemical analyzer. A second layer, e.g., applied to the working and auxiliary electrodes, was printed from a Prussian-Blue-graphite ink (e.g., C2070424P2, from Gwent Inc., Torfaen, UK). In some implementations, a third layer, which served as an insulator layer, can be printed over the substrate 101 with openings in the insulator layer that expose certain regions of the electrodes to facilitate the electrochemical detection (e.g., using DuPont 5036 Dielectric paste). For example, the insulator layer was used for coating the exposed silver-epoxy and Ag/AgCl contacts. After each printing step, the printed layers were cured at 80° C. for 20 min. Subsequently, the printed electrode system was attached to the PET substrate of the mouthguard body at the interior region of the mouthguard, as shown in FIG. 1A, using a double-sided adhesive. In this exemplary implementation, the electrochemical analyzer was connected to wires placed through holes inside the mouthguard body that were attached to Ag/AgCl contacts via a silver epoxy.

Lactate oxidase (LOx) was immobilized on the working electrode surface by electropolymeric entrapment in a poly (o-phenylenediamine) (PPD) film. This was accomplished, for example, using a 0.1 M phosphate buffer (pH 7.0) solution containing 10 mM o-Pd, 5 mM sodium sulfate, and 800 U/mL LOx, which was purged with nitrogen for 20 minutes. The mouthguard printable transducer was immersed in the polymerization solution. In this example, a potential of 0.55 V (vs Ag/AgCl) was subsequently applied for 1 min in order to grow the LOx-entrapped PPD film. Following the electropolymerization process, the exemplary sensor was rinsed and immersed in a 0.1 M phosphate buffer solution (pH 7.0) for 20 min to remove monomeric residues from the electrode surface as well as any non-bound enzyme. FIG. 1B shows the scheme of the exemplary modified working electrode transducer on the mouthguard platform for salivary lactate monitoring.

Exemplary electrochemical characterizations using the exemplary salivary electrochemical sensor device were performed in a buffer matrix. For example, the electrochemical performance of the exemplary mouthguard lactate sensor was evaluated in a 0.1 M phosphate buffer (pH 7.0) solution containing 20 mM NaCl (PBS) (mimicking the Cl concentration in human saliva). Chronoamperometric measurements of lactate at the exemplary PB-PPD-LOx biosensor device were carried out by stepping the potential to 0.042V (vs. Ag/AgCl) for 60 s after 2 min incubation in the sample solution. The current was sampled after 60 s. In these implementations, the applied potential was chosen based on cyclic voltammetry of the PB-carbon transducer, where the reduction of hydrogen peroxide produced the maximum current. Stability of the biosensor was examined in 0.5 mM lactate at 10 min intervals over a 2 h operation. The exemplary sensor was kept in 0.1 M PBS between such successive measurements.

Human saliva samples were collected from healthy volunteers at fasting conditions (e.g., at least 8 hr) using 'passive drool method', for example. The collected samples were kept at room temperature to allow their sediments to precipitate and the supernatant was used directly (without dilution) for electrochemical measurements. Due to the high viscosity of whole saliva samples, 50 μL of undiluted saliva aliquots were mixed with different lactate concentrations and vortexed for one min. The concentration of lactate in the saliva samples was determined via the standard addition method.

Electrochemical measurements of spiked saliva samples were carried out using the same conditions used in buffer matrix (e.g., $E_{APP}$=0.042V for 60 s). Prolonged measurements of such whole saliva samples were performed by changing the sample every 10 min to mimic the replenished in-mouth flow of saliva (unstimulated: 1 mL/min, stimulated: 2 mL/min). The exemplary sensor was kept in saliva between such successive measurements.

Exemplary results of these implementations are described. The lactate concentration of the human saliva varies depending on a person's metabolism and physical performance, with high correlations observed between blood (upto 17.3±1.9 mM) and salivary lactate levels (upto 1.6±0.4). Thus, a wide linear lactate detection range and a fast response time are essential for realizing continuous in-mouth monitoring of lactate in saliva. To address potential interferences in complex raw saliva samples, for example, the commonly used LOx enzyme was immobilized onto a printable PB-based transducer by entrapment within a PPD film. The exemplary PB-PPD-LOx biosensor, mounted on the mouthguard, was evaluated first in phosphate buffer medium.

Figure 2:
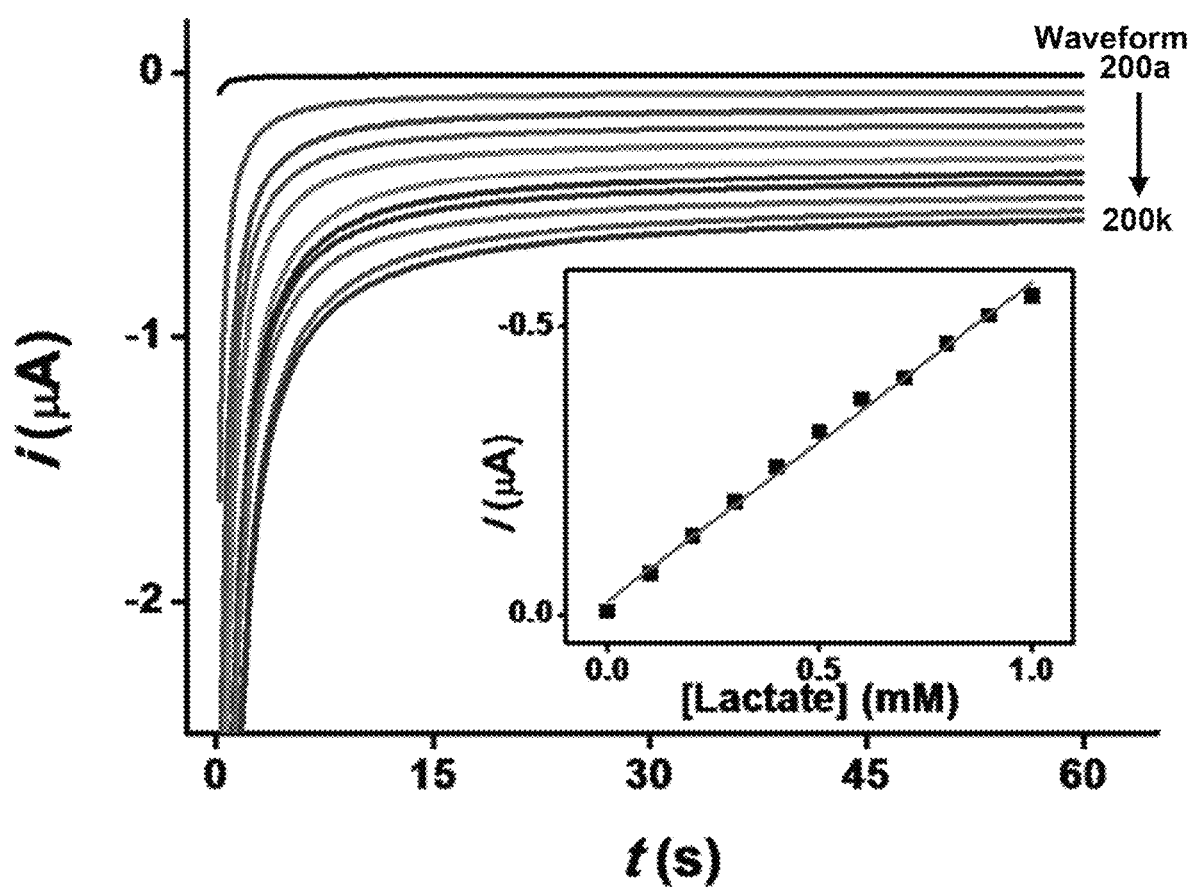
FIG. 2 shows a chronoamperographic data plot of exemplary results depicting dynamic range of the exemplary salivary electrochemical biosensor device in detecting lactate.

The dynamic concentration range was examined in response to increasing levels of lactate over the 0.1-1.0 mM lactate range using a low potential of 0.042V (vs. Ag/AgCl). FIG. 2 displays chronoamperograms for increasing concentrations of lactate in 0.1 mM increments in PBS medium (shown by waveforms 200b-200k in the data plot). These exemplary data indicate that the exemplary PB-PPD-LOx mouthguard biosensor displays a very high sensitivity toward lactate, with well-defined chronoamperograms and current signals proportional to the lactate concentration. The resulting calibration plot (shown in the inset of FIG. 2) exhibits high linearity (slope, 0.553 µA/mM; correlation coefficient, 0.994). It is also noted that there was a remarkably low background current (shown by waveform 200a in the data plot) associated with the extremely low operating potential. A low detection of around 0.050 mM can thus be estimated from the favorable signal-to-noise characteristics of the response for the 0.1 mM lactate (e.g., waveform 200b) (S/N=3). The exemplary PB-PPD-LOx mouthguard sensor can thus detect lactate effectively over the saliva lactate physiological range. For the exemplary data waveforms depicted in the chronoamperogram of FIG. 2, the exemplary implementations were performed with $E_{APP}$=0.042 V (vs Ag/AgCl) and a current sampling time of 60 s.

Figure 3:
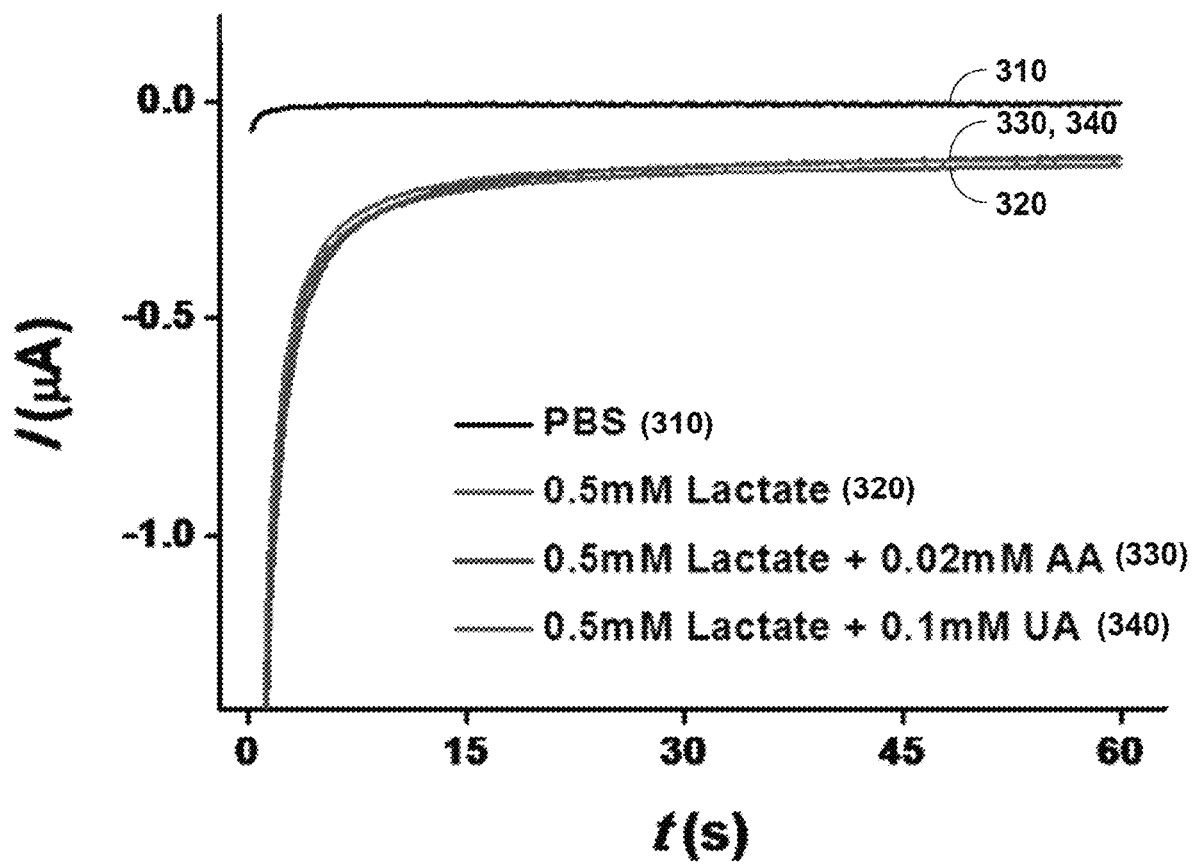
FIG. 3 shows a data plot of exemplary results showing the selectivity of the exemplary salivary electrochemical biosensor device in the presence of physiologically-relevant electroactive compounds.

Since the exemplary mouthguard biosensor would be exposed to complex raw saliva media in real world implementations, it should offer selective response in the presence of electroactive constituents (e.g., L-ascorbic acid, uric acid) that often interfere with the amperometric detection of lactate. The exemplary PB-PPD-LOx transducer-reagent-layer system is designed to minimize potential electroactive interferences by coupling the very low detection potential, e.g., offered by the PB surface, with the effective permselective behavior of the PPD layer. FIG. 3 displays the chronoamperometric response for 0.5 mM of lactate in the presence and absence of such physiological concentrations of ascorbic acid and uric acid. The selectivity of lactate was evaluated in the presence of physiological levels of the relevant electroactive constituents of human saliva, e.g., 100 µM uric acid (waveform 340 in FIG. 3), and 20 µM ascorbic acid (waveform 330 in FIG. 3). The selectivity of lactate was evaluated in the absence of AA and UA (waveform 320 in FIG. 3). Waveform 310 shows the response of PBS only. These exemplary data clearly indicate that these potential interferences have a negligible effect upon the lactate response (around 5% for both of AA and UA) and hence that the new mouthguard biosensor system offers high selectivity. In the data plot of FIG. 3, the exemplary results show the exemplary response to 0.5 mM lactate in 0.1 PBS and in the presence of common electroactive physiological interferents AA and UA, under the exemplary conditions as in FIG. 2.

Figure 4:
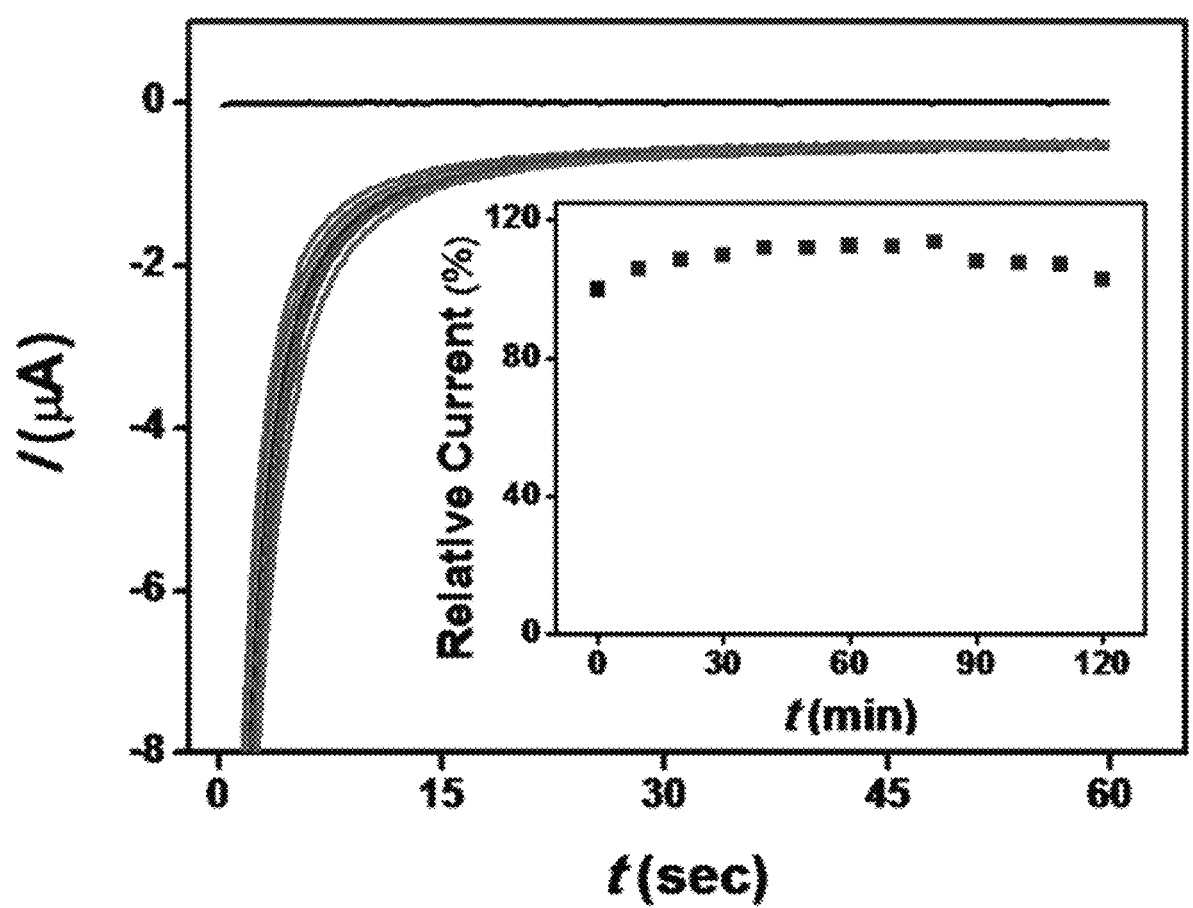
FIG. 4 shows a data plot of exemplary results showing the stability of the electrochemical response of the exemplary mouthguard biosensor to lactate over time.

High stability is another important requirement towards continuous in-mouth operation of the new mouthguard lactate biosensor. FIG. 4 shows a data plot of exemplary results showing the stability of the electrochemical response of the exemplary mouthguard biosensor to 0.5 mM lactate. In these exemplary implementations, the stability was initially evaluated over a continuous two-hour operation with repetitive measurements of 0.5 mM carried out every 10 min. The inset shows the time-course profile of the relative current, based on original current response (with the initial result at t=0 min normalized to 100%). For the exemplary implementations, the exemplary sensor was kept in 0.1 M PBS between such successive measurements. These exemplary data indicate a highly stable current response over the entire 2 hours operation. Other implementations have demonstrated the long-term stability of the sensor.

Figure 5:
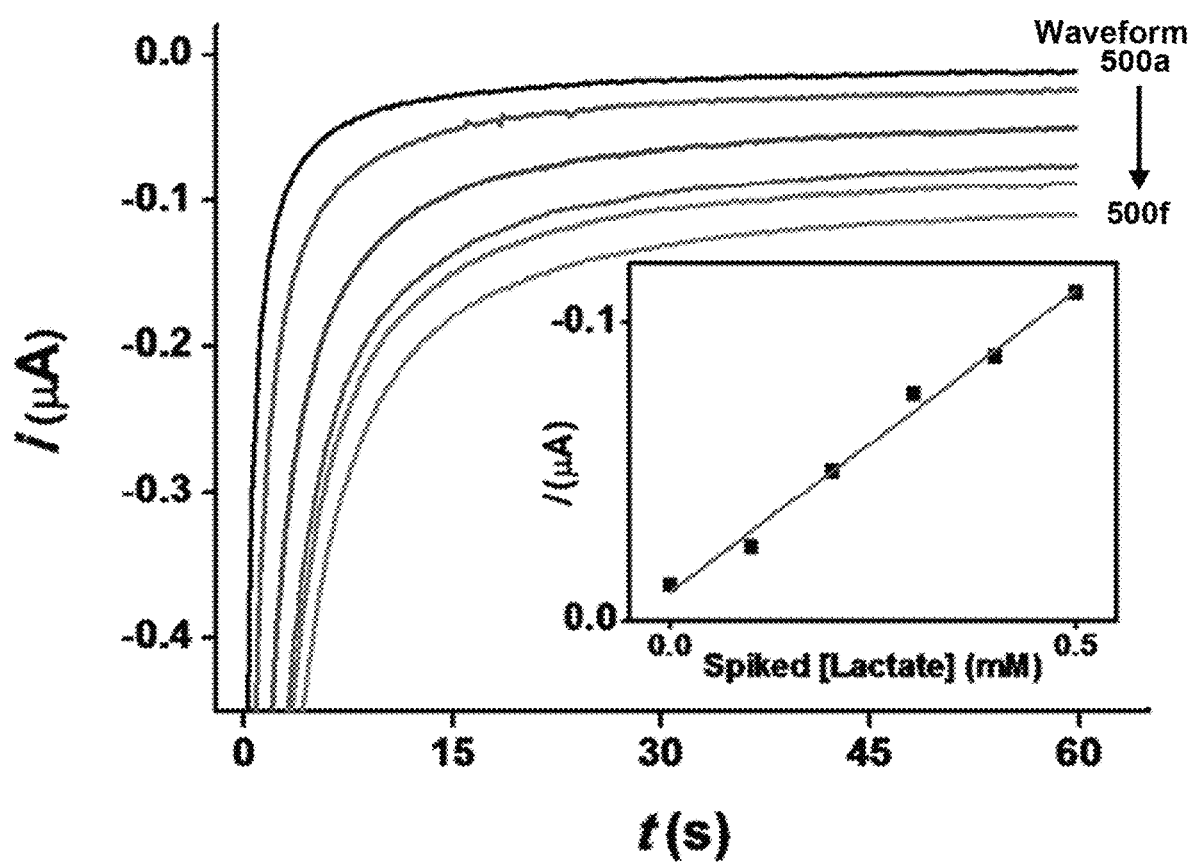
FIG. 5 shows a chronoamperographic data plot of exemplary results showing the response of the exemplary mouthguard biosensor to lactate in human saliva sample.

After the evaluation of the mouthguard biosensor in a synthetic buffer matrix, exemplary implementations were carried out by using human saliva samples. The response of the exemplary biosensor employed in the mouthguard to changing lactate levels was examined using unstimulated human saliva spiked 0.1-0.5 mM of lactate. As indicated from the well-defined chronoamperograms of FIG. 5, for example, the exemplary sensor responded favorably to such changes in the lactate level (e.g., shown by waveforms 500a-500f). The resulting calibration plot (shown in the inset) exhibited good linearity (slope, 0.202 µA/mM; correlation coefficient, 0.988). Other exemplary conditions were as in FIG. 2. The endogenous lactate level can thus be estimated to 0.010 mM, which is in the normal range in human saliva in rest without stimulation. The small current increments due to the lactate additions (vs those observed in the buffer media) may be attributed to the viscosity of the saliva samples that leads to slower diffusion, for example. No apparent change in the sensitivity or linear range were observed when testing the sensors at 37° C. (e.g., body temperature; not shown).

Figure 6:
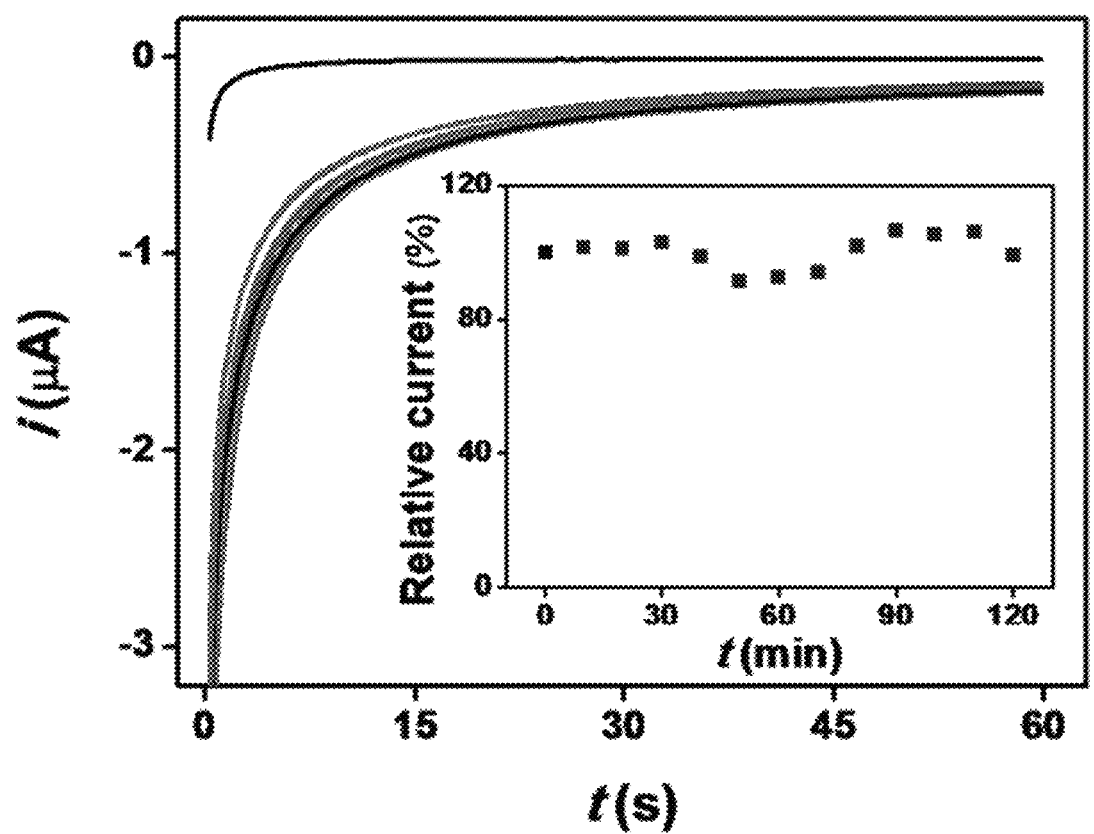
FIG. 6 shows a data plot of exemplary results showing the response stability of the exemplary mouthguard biosensor to a human saliva sample.

The exemplary implementations included stability assessments of the continuous exposure of the exemplary oral biosensory system to complex saliva media and potential degradation of the sensor response by co-existing proteins. FIG. 6 shows a data plot showing the response stability of the exemplary mouthguard biosensor to human saliva sample spiked with 0.5 mM lactate over time. In the implementations, repetitive measurements were carried out at 10 min intervals over a 2 hr period, replacing the saliva for each measurement to mimic the dynamic oral environment. The inset of FIG. 6 shows the relative current based on original current response (t=0). The exemplary sensor was kept in saliva between such successive measurements. Other exemplary conditions were as in FIG. 2. Only small variations of the current signal (e.g., ranging between 90% and 106% of the original response) were observed, for example, in this exemplary implementation. Such good stability reflects the protective action of the PPD coating against co-existing fouling constituents. Whenever needed, the disclosed mouthguard sensor system can be readily replaced during actual in-mouth operation to address further degradation of the sensor response by the saliva matrix.

The exemplary implementations of an exemplary embodiment of the non-invasive mouthguard biosensor devices (shown in FIGS. 1A and 1B) demonstrate continuous in-mouth monitoring of salivary metabolites. In one such implementation, amperometric measurements of lactate were performed using the exemplary PB-PPD-LOx biosensing platform. The disclosed technology can provide highly sensitive, selective, and stable lactate response in saliva samples, e.g., reflecting its low-potential signal transduction and rejection of co-existing electroactive and protein constituents. For example, such attractive performance of the mouthguard-based biosensing platform in detecting lactate in undiluted human salivary samples underscores the potential as a practical wearable device for continuous non-invasive physiological monitoring of the fitness state of individuals.

Other biochemicals present in saliva can also be used in other exemplary implementations of the disclosed biosensor devices. In some examples, glucose can also be electrochemically detected and utilized in a printed biofuel cell application.

Exemplary Glucose Biosensors

Figure 7:
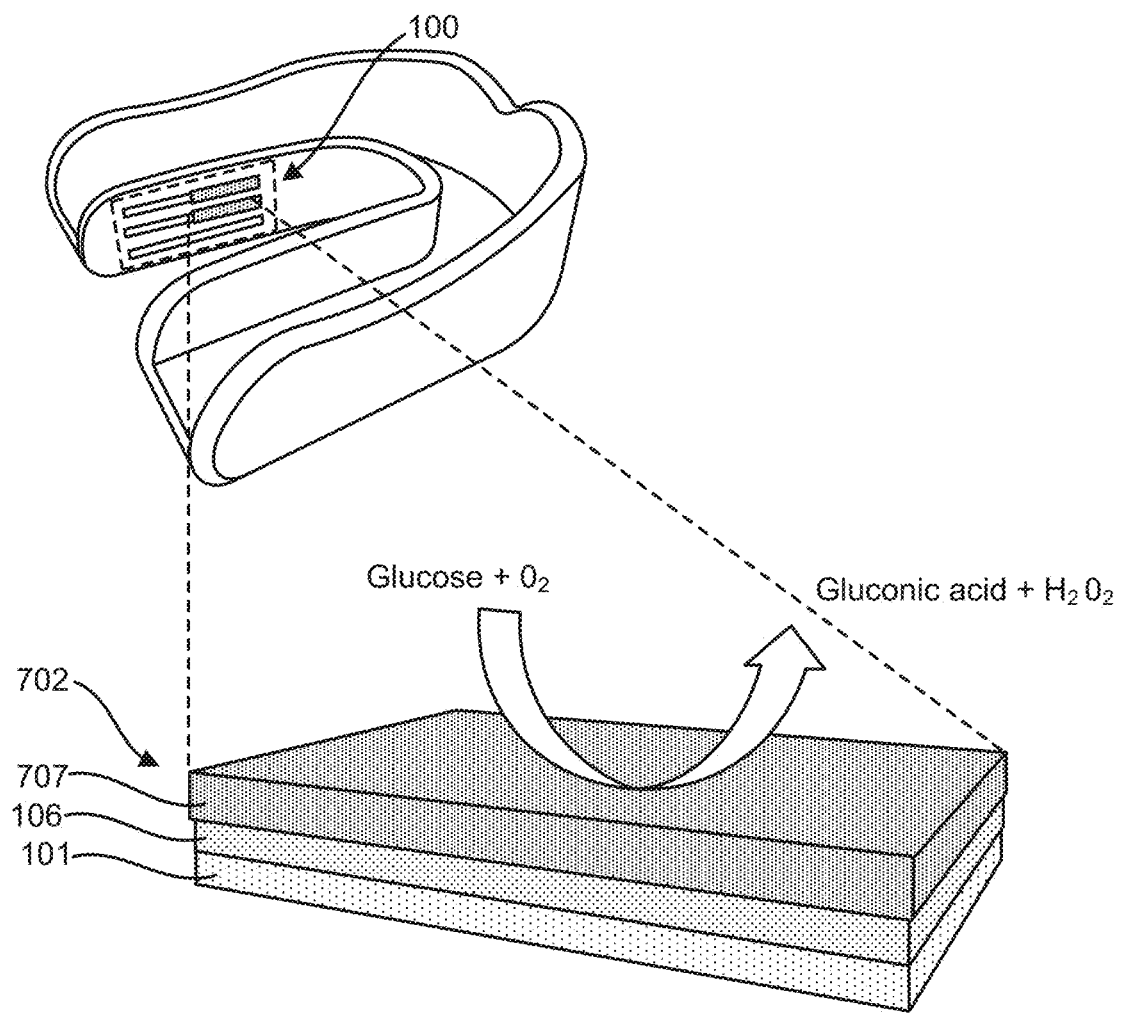
FIG. 7 shows a schematic illustration of an exemplary salivary electrochemical sensor device employed in a mouthguard, including a blow-up illustration of an exemplary electrode configuration of the device designed for salivary glucose monitoring.

FIG. 7 shows a schematic illustration of the exemplary salivary electrochemical sensor device 100 employed in a mouthguard and a blow-up illustration of an exemplary electrode configuration 702 of the biosensor device 100 for salivary glucose monitoring. As shown in FIG. 7, the working electrode and the reference electrode of the exemplary biosensor device 100 is configured in an electrode structure 702. The electrode structure 702 includes the electrically conductive material 106 disposed on the substrate 101, in which the electrically conductive material 106 is coated by an electrochemical transducer layer 707 including a catalyst corresponding to glucose to cause a electrochemical reaction that is detectable at the electrodes 102. For example, in some implementations, the chemical substance includes a catalyst to selectively catalyze a corresponding analyte in the saliva to cause or facilitate a reaction that produces a detectable signal at the electrodes 102. In the example shown in FIG. 7, the catalytic chemical substance contained in the electrochemical transducer layer 707 includes glucose oxidase (GOx), which can catalyze a redox reaction with glucose (e.g., the selected analyte in the saliva to be detected) that generates the electrical signal at the electrodes 102.

Figure 8:
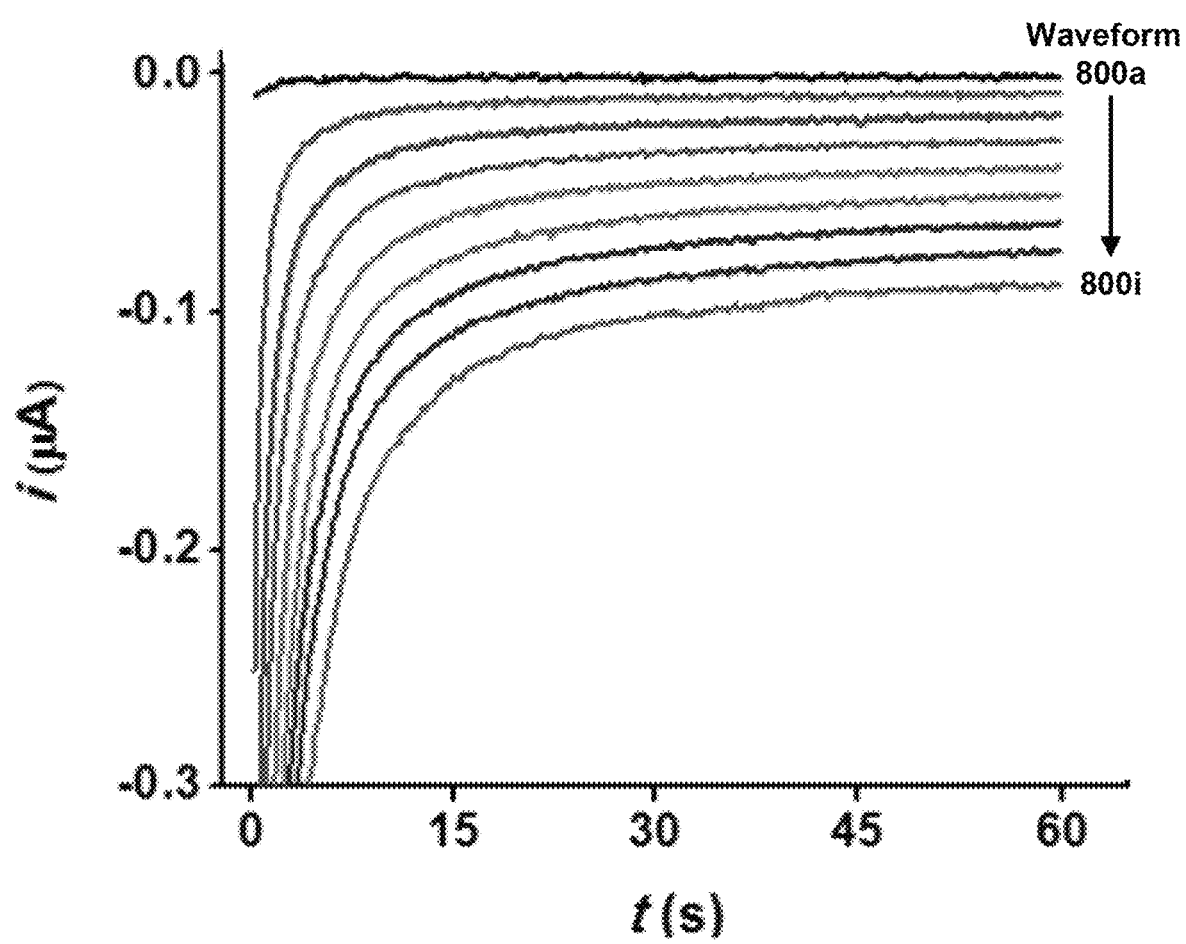
FIG. 8 shows a chronoamperographic data plot of exemplary results obtained for increasing glucose concentration by an exemplary salivary electrochemical biosensor device.

FIG. 8 shows a chronoamperographic data plot of exemplary results obtained for increasing glucose concentration in increments (shown by waveforms 800a-800i). In the exemplary implementations performed to obtain the data, the transducer layer 702 included GOx enzyme immobilized onto a printable PB-based transducer by entrapment within a PPD film. Exemplary conditions in these exemplary implementations were similar to those associated with FIG. 2. As shown by FIG. 8, the exemplary PB-PPD-GOx mouthguard sensor can thus detect glucose effectively over the saliva lactate physiological range.

Exemplary Integrated Electrochemical Sensors, Biofuel Cells and Electronics

Figure 9:
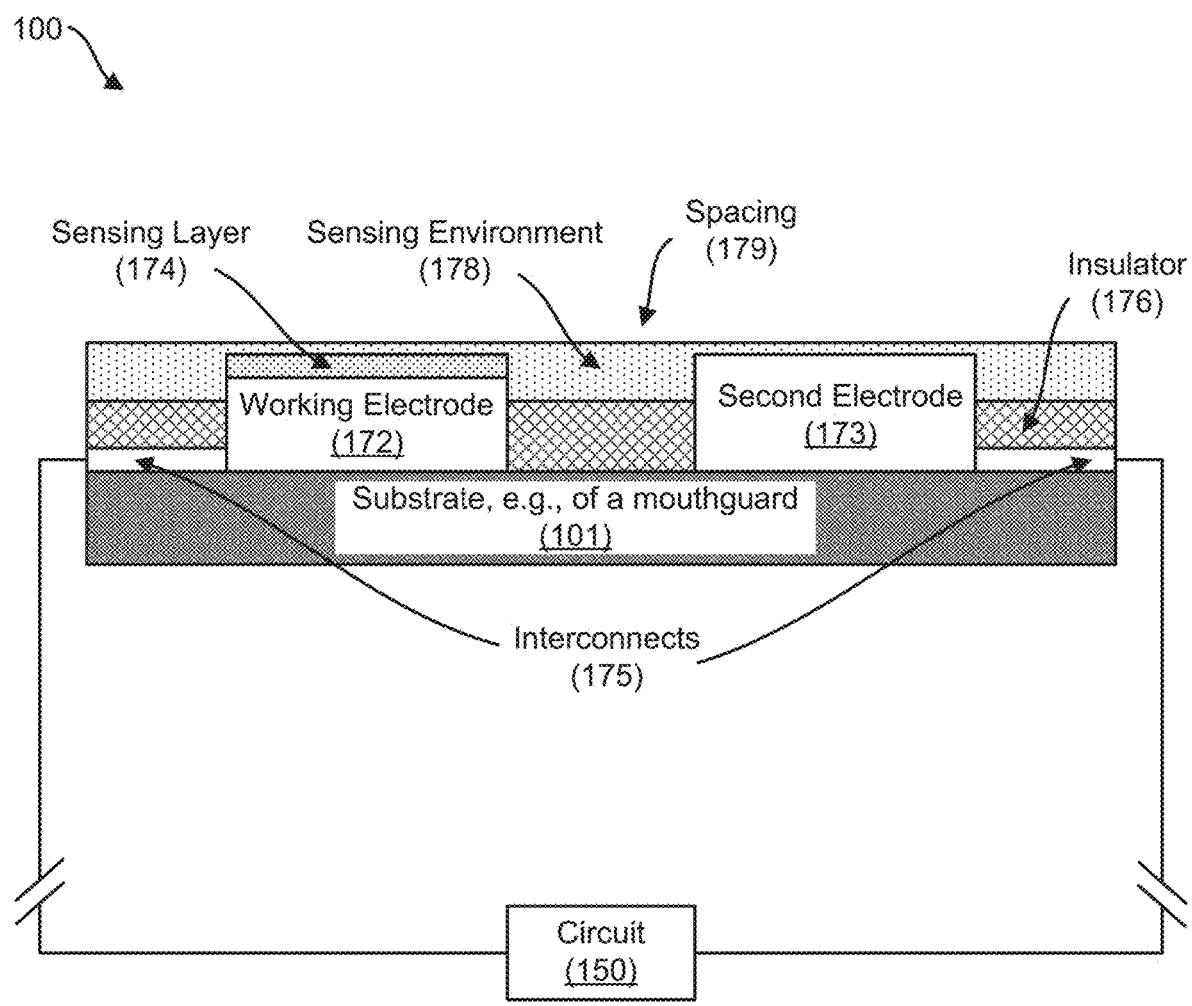
FIG. 9 shows a block diagram of an exemplary electrochemical sensor device of the disclosed technology that can be implemented in exemplary mouthguard devices, such as those shown in FIG. 1A and FIG. 7A, for example.

FIG. 9 shows a block diagram of the exemplary electrochemical sensor device 100, which can be implemented in a mouthguard, as shown in FIGS. 1A and 1B and FIG. 7, for example. The electrochemical sensor device 100 includes the substrate 101, which includes an electrically insulative material, and which can be configured in a form-fitted mouthguard or other mouthguard device. In the example shown in FIG. 9, the electrochemical sensor device 100 includes a working electrode 172 and a second electrode 173 disposed on the substrate 101, in which the working electrode 172 and the second electrode 173 are separated from one another by a spacing 179. The electrochemical sensor device 100 can include an insulator layer or structure 176, e.g., which can provide further structural support for the device 100 and protect the electrical signal integrity of conducted electrical signals through the electrodes and interconnects or conduits 175. For example, the electrode configuration of the disclosed electrochemical sensor devices can be designed based on the type of target analyte to be sensed and the type of detection methodology, e.g., amperometry, voltammetry, potentiometry, and/or electrochemical impedance spectroscopy, or other electrochemical analysis technique, to be employed. In some examples, the electrochemical sensor device 100 can be configured to detect charged analytes, e.g., using potentiometry. In some examples, the electrochemical sensor device 100 can be configured to detect self-oxidizing analytes on a bare working electrode 172, in which the device 100 includes a third electrode positioned between the working electrode 172 and second electrode 173; and the second electrode 173 and the third electrode can serve as a counter electrode and a reference electrode, respectively. In some embodiments, for example, the electrochemical sensor device includes an array of electrode contingents, e.g., such as an array of working electrodes and reference electrodes, and/or counter electrodes.

In some examples, as shown in the diagram of FIG. 9, the working electrode 172 includes an electrochemical sensing layer 174 to sustain a redox reaction to produce a detectable electrical signal that can be detected using, for example, amperometry and/or voltammetry. In operation, the sensing environment 178 (e.g., fluid or saliva) containing a target analyte makes contact with the surface of the exemplary electrochemical sensor device 100 such that the sensing environment 178 can immerse the spacing between the working electrode 172 and the second electrode 173. The electrochemical sensing layer 174 provides a reaction agent (e.g., a catalyst) that can facilitate a redox reaction with the target analyte (e.g., such as a particular molecule or substance) in the fluid (e.g., saliva) that produces charge carriers sensed by the working electrode 172. The electrochemical sensing layer 172 can be structured to include a catalyst and an electroactive redox mediator. In some examples, the target analyte can be oxidized by the catalyst, releasing electrons in the process, which gives rise to an electrical current that can be measured between the working electrode 172 and second electrode 173. For example, the electroactive redox mediator can facilitate the transfer of electrons between the working electrode 172 and the active site of the catalyst. The electrochemical sensing layer 174 can be configured to the working electrode 172 by, for example: (i) the catalyst is dispersed within the material of the working electrode 172; (ii) the catalyst is coated as a layer on the surface of the working electrode 172, e.g., in which the catalyst is covalently bonded or electrostatically anchored to the surface; or (iii) the catalyst entrapped by an electropolymerized conducting polymer formed on the surface of the working electrode 172, and/or by a selectively permeable scaffold structure, e.g., such as Nafion or chitosan, formed on the surface of the working electrode 172. In exemplary implementations including the electroactive redox mediator, for example, the electroactive redox mediator can be configured in the electrochemical sensing layer 174 along with the catalyst by the same exemplary configuration.

As shown in the diagram of FIG. 9, the electrochemical sensor device can be electrically coupled to the electrical sensor circuit 150 to the electrodes via the electrical interconnects 175. For example, the sensor circuit 150 can be configured to apply excitation waveforms and/or transduce the electrical signals generated by the electrochemical electrodes of the electrochemical sensor device 100 upon excitation. In some examples, the sensor circuit 150 can include a signal conditioning unit and communication unit to transmit the acquired data to an external device, e.g., which can include a display or other interface to display the results to the wearer of the mouthguard or other user, e.g., such as a coach, trainer, or physician, in real-time. The sensor circuit 150 can be structured to include, but not limited to, a potentiostat (e.g., to realize amperometric and voltammetric measurements) or a galvanostat (e.g., to realize potentiometric measurements). In some embodiments, for example, the electrochemical sensor device 100 can include electrically conductive contact pads coupled to the interconnects 175 to provide a conductive surface to electrically interface an external circuit or device to the electrodes of the electrochemical sensor device 100.

The disclosed technology can be used for continuous in-mouth salivary analyte monitoring in an integrated platform, which can include miniaturization and integration of the amperometric circuits and electronics for data acquisition, processing, and wireless transmission, as well as critical assessment of all potential toxicity and biocompatibility concerns. The amperometric mouthguard biosensing concept can readily be implemented towards salivary monitoring of other clinically-relevant metabolites and stress markers, hence offering useful insights into the wearer's health and performance and considerable promise for diverse biomedical and fitness applications.

For example, the disclosed integrated sensor-fuel cell electronic platform can be utilized for real-time electrochemical performance monitoring. In some embodiments, for example, the disclosed integrated platform includes advanced wearable biosensing tags in a mouthguard with integrated functional components within a form factor that is suited to the human body, e.g., including a structure that supports functional elements and transmits the item to be sensed, the sensors themselves, microelectronic circuitry to process and transmit the sensor signal, a power source, and wiring to interconnect the various components. In some examples, discrete electronics and microfabricated electrodes can be used in such devices.

Figure 10A:
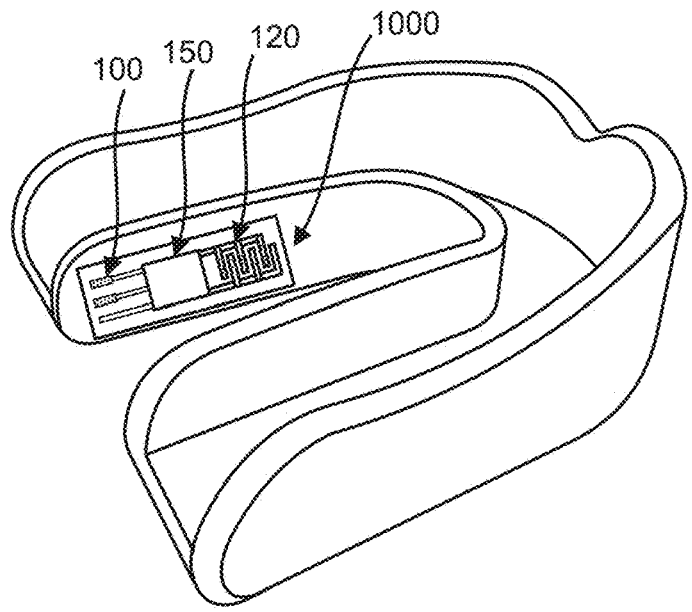
FIG. 10A shows a schematic illustration and diagram of an exemplary integrated biosensor, biofuel cell, and electronic device platform employed in a mouthguard.

FIG. 10A shows a schematic illustration and diagram of an exemplary integrated biosensor, biofuel cell, and electronics platform 1000 capable of being employed in a mouthguard. The platform 1000 includes an exemplary embodiment of the electrochemical biosensor device 100 and an exemplary embodiment of the biofuel cell device 120, which are electrically interfaced by an exemplary electrical circuit 150. In some implementations, for example, the electrical circuit 150 can include a DC/DC converter that tracks the power coming from the biofuel cell 150, e.g., which is related to the underlying analyte concentration for sensing by the biosensor 100, to achieve self-powered operation of the integrated sensor-fuel cell platform 1000. For example, the exemplary biosensor device 100 and biofuel cell device 120 can be integrated in the mouthguard by fabricating one or more salivary analyte biosensors (e.g., to detect glucose, lactate, and/or uric acid or other) and biofuel cell to extract energy from one or more salivary chemical fuel substances, e.g., as previously described. In the exemplary integrated design, transducer ink materials and bioelectronic reagent layers can be optimized during such fabrication processes. The exemplary integrated biosensor, biofuel cell, and electronics device platform 1000 can include discrete component based devices and interfacing, e.g., including the design of electronics for an anatomically-miniaturized electrochemical analyzer and the associated electronic interfaces, digitization circuitry, and communications. The overall assembly of electronics can be produced into a mouthguard form factor.

Figure 10B:
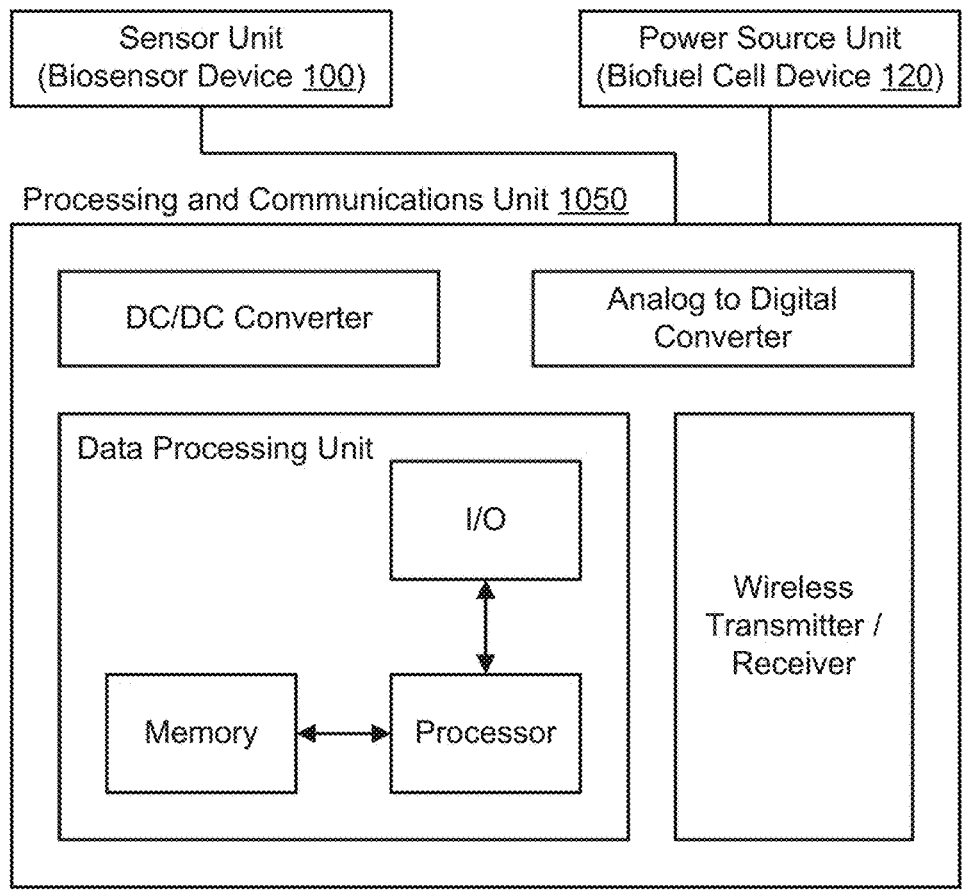
FIG. 10B shows a block diagram of an exemplary electronic processing and communications unit of the integrated platform.

FIG. 10B shows a block diagram of an exemplary electronic processing and communications unit 1050 of the integrated platform 1000. For example, the processing and communications unit 1050 of FIG. 10B can included in or utilized as the electrical circuit 150, e.g., such as shown in FIG. 10A. As shown in FIG. 10B, the processing and communications unit 1050 includes analog-to-digital converters and signal conditioning and processing circuitry, which can interface with the biofuel cell device 120 as a power source for the unit 1050. The processing and communications unit 1050 includes a data processing unit capable of signal processing and communications (e.g., to external devices), and DC/DC converters and/or signal conditioning circuits. The data processing and communications unit 1050 includes a wireless transmitter/receiver unit to wirelessly transmit data processed by the data processing unit or conditioned by the signal conditioning circuits to an external device.

The data processing unit of the unit 1050 can include a processor to process data and a memory in communication with the processor to store data. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another entity or to a user. In some implementations, the data processing unit can be implemented by a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The data processing unit can include an input/output unit (I/O) that can be connected to an external interface, source of data storage, or display device. For example, various types of wired or wireless interfaces compatible with typical data communication standards can be used in communications of the data processing unit via the wireless transmitter/receiver unit, e.g., including, but not limited to, Universal Serial Bus (USB), IEEE 1394 (FireWire), Bluetooth, IEEE 802.111, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of an external device. For example, an external display device can be configured to be in data communication with the data processing unit, e.g., via the I/O, which can include a visual display device, an audio display device, and/or sensory device, e.g., which can include a smartphone, tablet, and/or wearable technology device, among others.

In some implementations, for example, the data processing unit can include an electrochemical analyzer on-board the processing and communication unit 1050. For example, the electrochemical analyzer can include electrical or electronic components capable to acquire and process the data coming from a potentiostat device or galvanostat device. In some implementations of the processing and communication unit 1050, for example, the unit 1050 can include an internal or additional power supply such as a battery to power the modules of the unit 1050.

Some exemplary specifications of two exemplary embodiments of the integrated platform 1000 are provided in Table 1. Other embodiments of the integrated biosensor, biofuel cell, and electronics device platform 1000 can be configured to one or more of the exemplary specifications shown in Table 1, or configured to other specifications not shown in Table 1.

TABLE 1

| Exemplary Performance Metrics | Specifications Example 1 | Specifications Example 2 |
| --- | --- | --- |
| Metabolites | Glucose, lactate | Glucose, lactate |
| Data Acquisition | <15 s | <5 s |
| Power consumption (system) | <5 mW | <1 mW |
| Storage | 6 months RT | >6 months RT |
| Operating Temperature | 10-50 C. | 5-60 C. |
| Storage Temperature | 5-60 C. | 0-70 C. |
| Sensitivity | >0.4 µA/mM (metabolite) | >1 µA/mM (metabolite) |
| Stability | >8 hrs continuous sensing | >24 hrs continuous sensing |
| Selectivity | <10% current level deviation from any phys. interferent | <5% current level deviation from any phys. interferent |
| Response Time | <5 s | <1 s |
| Limit of Detection | Lowest physiological level | Lowest physiological level |
| Detection RSD & R^2 | <10%, >0.90 | <5%, >0.95 |
| Hysteresis | <10% | <5% |
| Precision | <10% | <5% |
| Batch-to-Batch Variation | <10% | <5% |

The disclosed integrated platform can be fabricated using processes for additively manufacture of exemplary mouthguard devices of the disclosed technology to the exact shape and configuration for the wearer and the desired biosensing task. For example, an additive manufacturing platform can be applicable to a variety of wearable devices that are fabricated, on demand, to an arbitrary form factor and configuration. For example, a general manufacturing platform capable of digital, additive assembly can open up the range of wearable systems. Such a manufacturing platform can allow for rapid transition from design to device for many different types of sensors, as well as enabling personalization.

Exemplary Uric Acid Biosensors

In some implementations, the disclosed wearable mouth-based salivary biosensors can be utilized to detect salivary uric acid for diagnosis and monitoring treatment of hyperuricemia. The following describes exemplary designs and in vitro characterizations of the exemplary mouthguard-based biosensor used in implementations of continuous in-mouth monitoring of uric acid.

Figure 11A:
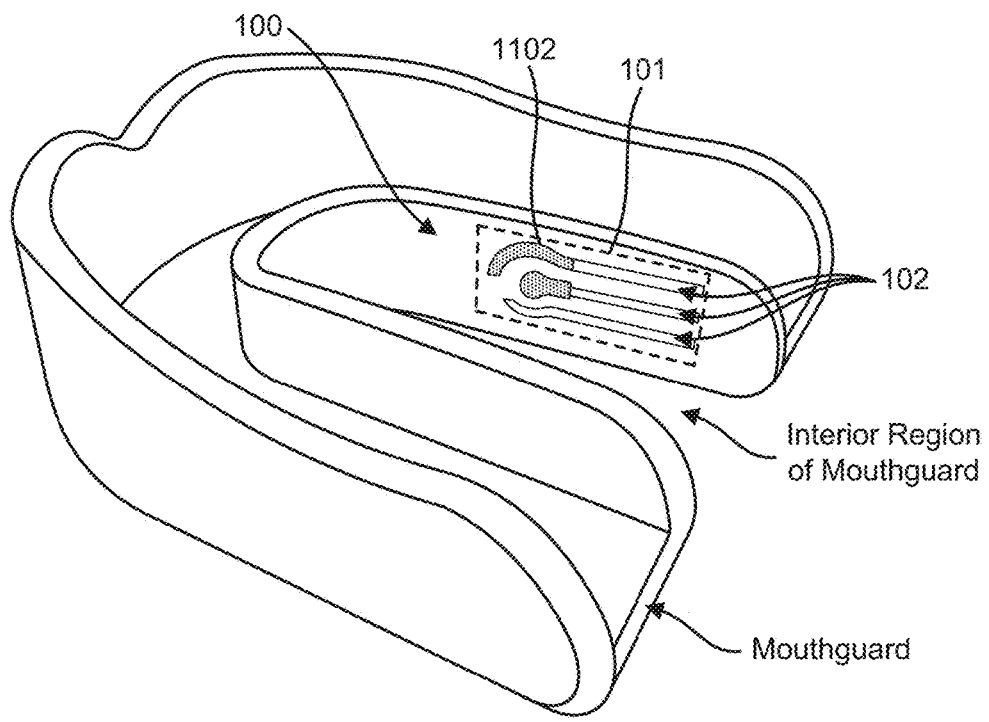
FIG. 11A shows a photograph of an exemplary screen-printed electrochemical sensor of the disclosed technology integrated with a mouthguard.

FIG. 11A shows a photograph of an exemplary screen-printed electrochemical sensor integrated with a mouthguard. In the example shown in FIG. 11A, the electrochemical sensor 100 is produced as a screen-printed electrochemical sensor on the substrate 101 that can be attached or integrated into the mouthguard. As shown in FIG. 11A, the working electrode and the reference electrode of the biosensor device 100 is configured in an electrode structure 1102.

Figure 11B:
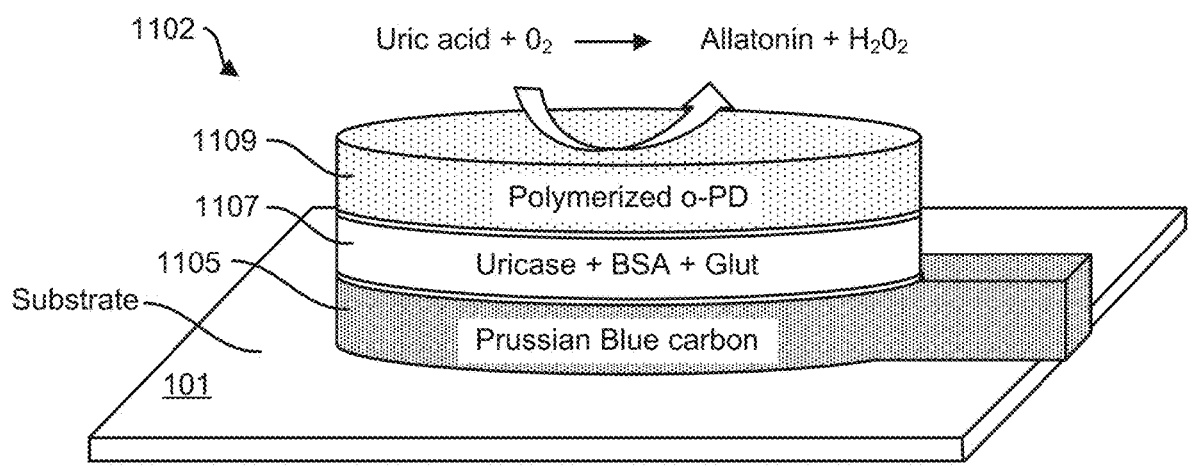
FIG. 11B shows a schematic illustration of an exemplary electrode configuration of an exemplary salivary uric acid biosensor including a reagent layer of the working electrode on a substrate.

FIG. 11B shows a schematic illustration of an exemplary electrode configuration 1102, which can be utilized in as the working electrode of the electrodes 102 of the device 100. The example shown in FIG. 11B can be included in embodiments of a salivary uric acid biosensor of the disclosed technology. The structure of the modified electrode 1102 can include an electrode 1105 including an electrically conductive material that is electrochemically inert, e.g., Prussian Blue carbon, disposed on a substrate (e.g., PET substrate). The modified electrode 1102 can include a reagent layer 1107 of the immobilized enzyme (e.g., uricase, mixed with BSA and Glut) on the electrode 1105. The modified electrode 1102 can include an entrapment layer 1109 (e.g., OPD) to maintain the immobilized enzyme to the electrode.

Exemplary implementations of the exemplary mouthguard uric acid biosensor included the following chemicals and reagents. Uricase, 1,2-phenylenediamine (o-Pd), L-lactic acid, L-ascorbic acid (AA), uric acid (UA), sodium sulfate, sodium chloride, calcium chloride, potassium chloride, citric acid, potassium thiocyanate, ammonium chloride, potassium monobasic, potassium dibasic, bovine serum albumin (BSA), and glutaraldehyde (Glut) solution were obtained and were used without further purification or modification. Ultrapure water (18.2 MΩ·cm) was employed in the exemplary implementations.

The exemplary implementations of the exemplary mouthguard lactate biosensor included the following instrumentation. A MPM SPM semi-automatic screen printer was used for printing the electrodes. The sensor patterns were designed using AutoCAD, and stencils were patterned on 75 µm-thick stainless steel stencils. A CH Instruments model 621A electrochemical analyzer was employed for the electrochemical measurements.

The exemplary mouthguard-based salivary electrochemical sensor device shown in FIGS. 11A and 11B can be fabricated using the fabrication techniques previously described, and integrated into a mouthguard. For this embodiment, for example, the working electrode is chemically modified with an enzyme and anti-biofouling membrane. For example, the uricase enzyme is immobilized in the following manner. First, uricase (e.g., 3.0 mg) can be mixed with BSA (e.g., 2 mg) and glutaraldehyde (e.g., 1 µL of stock solution) in potassium phosphate buffer (e.g., 200 µL). The mixed solution (e.g., 3 µL of the mixed solution) can be drop-casted on the working electrode and dried (e.g., for 30 min). Next, o-phenylenediamine (OPD) can be electropolymerized to reject biofouling and interference effect from in saliva. This can be accomplished by applying 0.6 V (vs Ag/AgCl) for 5 min to a 0.1 M phosphate buffer (pH 7.0) solution containing 10 mM o-Pd, 5 mM sodium sulfate, which can be purged with nitrogen (e.g., for 20 minutes before use). The schematic of FIG. 11B shows the chemical constitution of the exemplary modified working electrode on the mouthguard platform.

The electrochemical performance of the exemplary salivary uric acid biosensor integrated with the mouthguard was evaluated in artificial saliva, which has similar electrolyte concentration with human saliva. For example, normal salivary uric acid level is from 250 uM to 350 uM. To cover hyperuricemia patient's uric acid level, the dynamic concentration range was examined in current response over 0-1 mM uric acid measured at −0.3V steps (vs. Ag/AgCl). For example, the artificial saliva was prepared by dissolving 5 mM of NaCl, 1 mM of CaCl$_2$, 15 mM of KCl, 1 mM of citric acid, 1.1 mM of KSCN, 4 mM of NH$_4$Cl in distilled water. Chronoamperometric measurements of uric acid at the exemplary PB-PPD-Uricase biosensor were carried out by stepping the potential to −0.3V (vs. Ag/AgCl) for 60 s after 1 min incubation in the sample solution. In the exemplary implementations, the applied potential was chosen from cyclic voltammetry of the biosensor where the response of uric acid showed distinguishable current response within physiological range in saliva. Stability of the biosensor was examined in 350 μM uric acid at 10 min intervals over a 2 hr operation. The exemplary sensor was kept in artificial saliva between such successive measurements. Selectivity was evaluated in 350 μM uric acid in artificial saliva in the presence of relevant electroactive physiological interferents.

Figure 12A:
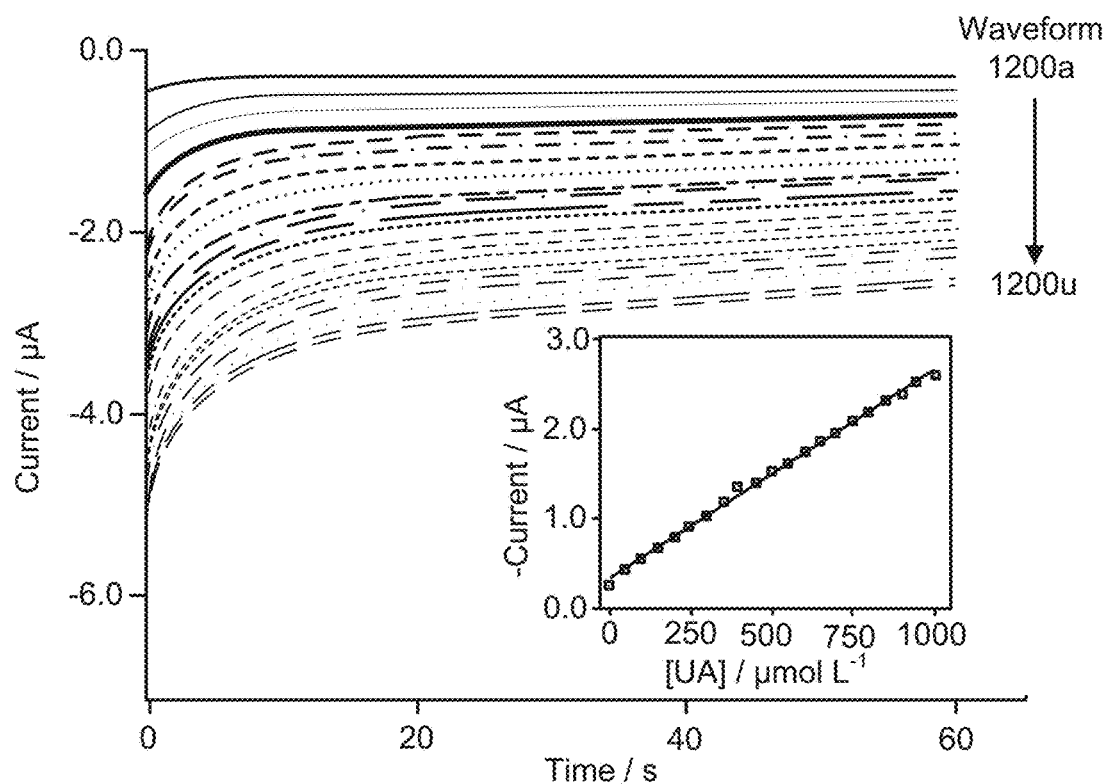
FIG. 12A shows chronoamperographic data depicting the response of an exemplary uric acid biosensor obtained for increasing uric acid concentrations.
Figure 12B:
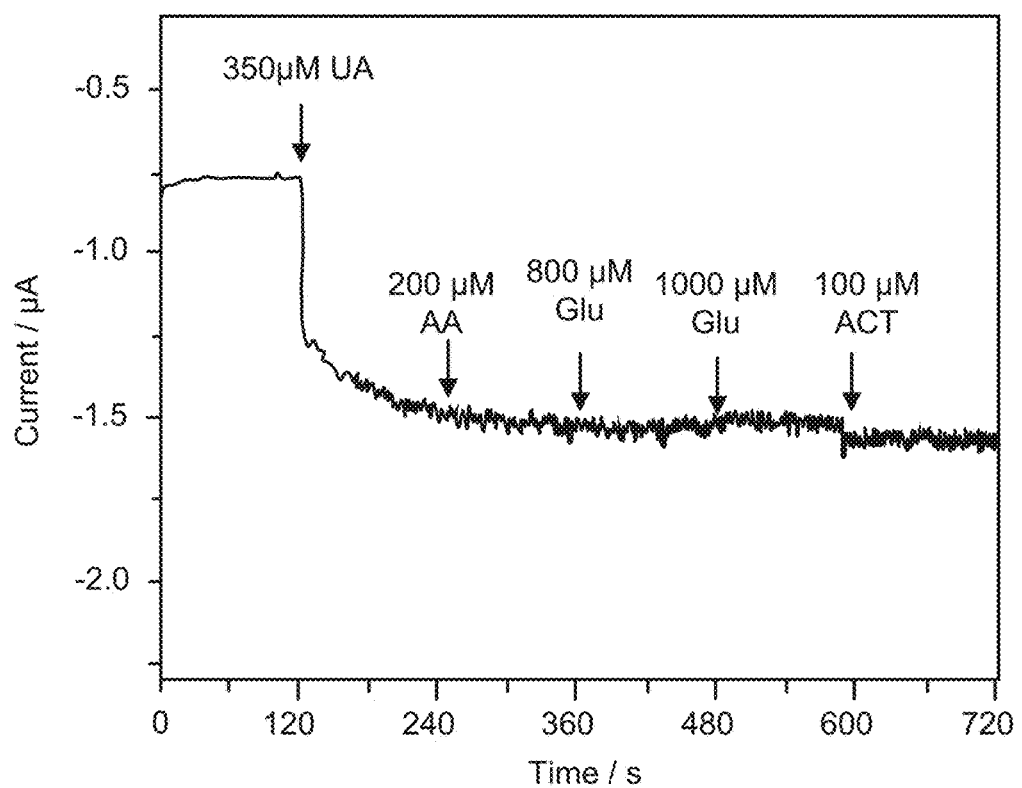
FIG. 12B shows exemplary results of the response of the exemplary biosensor to uric acid in the presence of common electroactive physiological interferents.
Figure 12C:
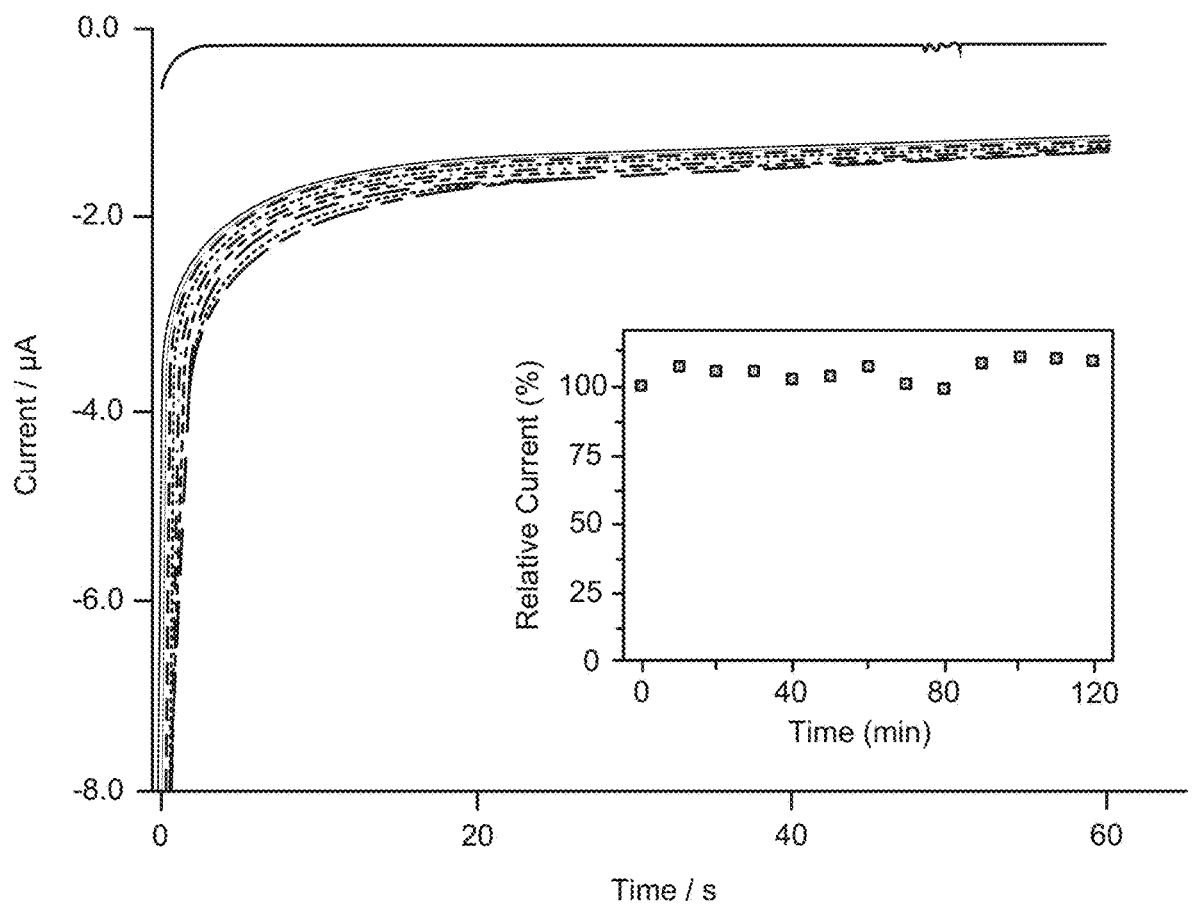
FIG. 12C shows exemplary results of the electrochemical response stability of the exemplary biosensor to uric acid over time sampled at multiple intervals.

FIG. 12A shows a chronoamperographic data plot depicting the response of the exemplary biosensor obtained for increasing uric acid concentrations with 50 μM increments up to 1 mM (shown by waveforms 1200a-1200u). The resulting calibration curve is shown in the inset of FIG. 12A. FIG. 12B shows exemplary results of a selectivity test depicting the response to 350 μM uric acid in the presence of common electroactive physiological interferents. FIG. 12C shows exemplary results depicting the electrochemical response stability to 350 μM uric acid over a 2 h operation with 10 min intervals. The inset of FIG. 12C shows the relative current, based on original current response (t=0 s). The exemplary sensor was kept in artificial saliva between such successive measurements. The implementations were performed with $E_{app}$=−0.3 V (vs. Ag/AgCl) and a current sampling time of 60 s.

The exemplary data indicates the exemplary PB-PPD-Uricase biosensor is very sensitive to uric acid and has wide linear range, with well-defined chronoamperograms and current response proportional to uric acid concentration (as shown in inset calibration plot of FIG. 12A). For example, since a saliva matrix has so many interferents, selectivity should be secured for real-application in human saliva sample. The selectivity was evaluated in the presence of physiological levels of the relevant electroactive species of human saliva including glucose, lactate, ascorbic acid, and acetaminophene. As shown in FIG. 12B, the exemplary biosensor showed favorable response to 0.35 mM uric acid, while response to other electroactive interfering species is negligible. For some implementations, for example, to monitor continuously the effect of treatment in acute gout, stability of the biosensor was examined for 2 hours with 10 min intervals in response to 0.35 mM uric acid. FIG. 12C displays retained response after 2 hr operation, the stable response is attributed by the BSA and glutaraldehyde cross-linking reaction as well as PPD layer, which help intact immobilization of enzyme even for 2 hr measurement.

Exemplary implementations of the exemplary mouthguard uric acid biosensor included measurements in undiluted human saliva. Due to proteins such as mucin and viscosity of untreated human saliva, electrochemical measurement can be quite challenging to reject bio-fouling on electrode surface. Samples were collected from healthy volunteers by using the 'passive drool' technique to obtain exemplary measurements in undiluted human saliva. The collected samples were directly used for electrochemical measurement without any treatment. The concentration of uric acid in the saliva samples was determined via the standard addition method by applying same conditions used in artificial saliva (e.g., $E_{APP}$=−0.3V for 60 s). For continuous measurement in real saliva sample, signal was measured every 20 min, and the sample was replaced at every measurement considering the flow rate of saliva in mouth (e.g., unstimulated: 1 mL/min, stimulated: 2 mL/min). For example, the sensor was immersed in saliva between such successive runs. The chronoamperometric response in human saliva to uric acid is obtained by spiking 0.1-0.5 mM of uric acid via standard addition method.

Figure 13A:
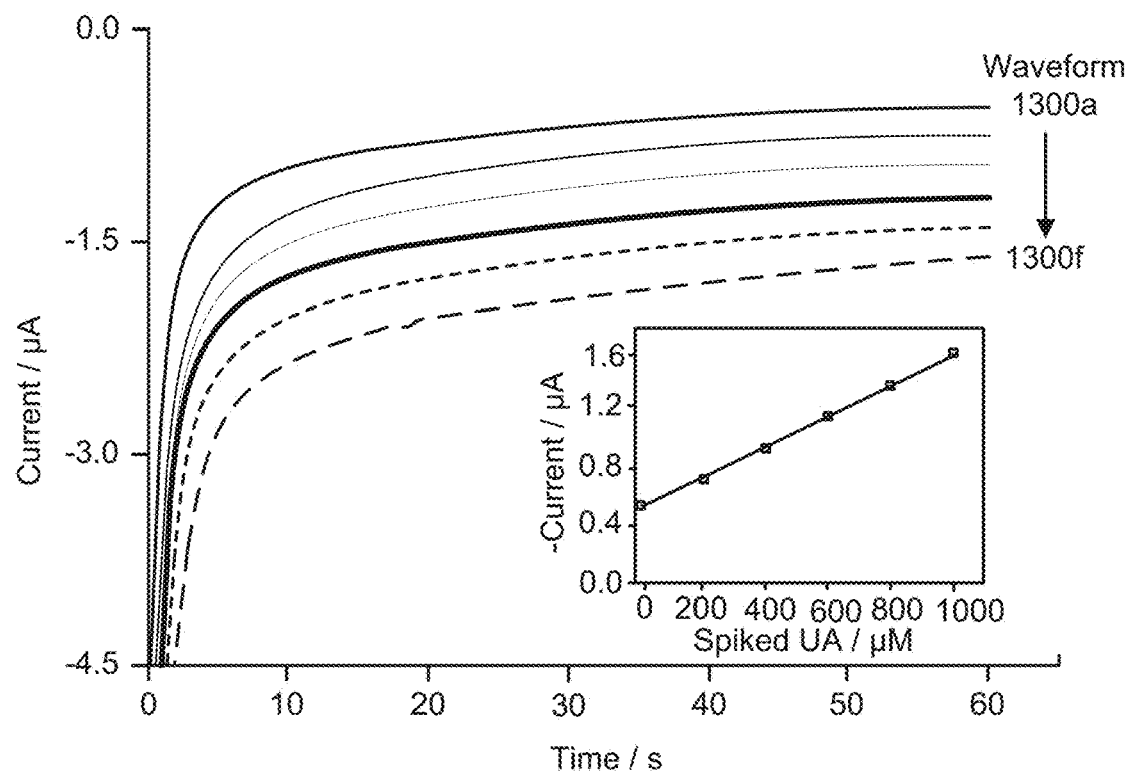
FIG. 13A shows chronoamperometric data depicting the electrochemical response of an exemplary uric acid biosensor in undiluted human saliva.
Figure 13B:
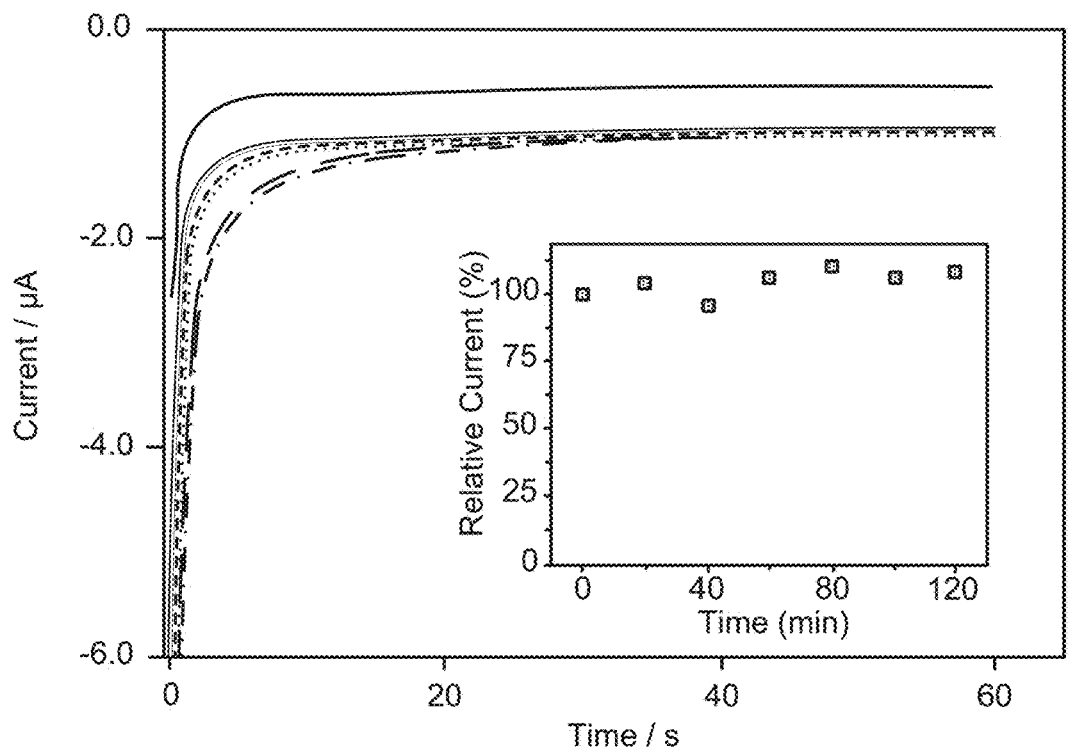
FIG. 13B shows a data plot depicting the stability of the response data in human saliva.

FIG. 13A shows chronoamperometric data depicting the electrochemical response of the exemplary PB-PPD-Uricase biosensor in undiluted human saliva spiking different concentrations of uric acid with 0.2 mM increments (shown by waveforms 1300a-1300f). The resulting calibration curve is shown in the inset of FIG. 13A. FIG. 13B shows a data plot depicting the stability of the response in human saliva sample spiked with 350 μM uric acid. Repetitive measurements were carried out at 20 min intervals over a 2 hr period. The inset in FIG. 13B is the relative current based on original current response (t=0 s). The exemplary sensor was kept in saliva between such successive measurements, and the exemplary conditions included $E_{APP}$=−0.3 V (vs. Ag/AgCl) and t=60 s.

As illustrated in FIG. 13A, the biosensor response favorably to different concentrations of uric acid in undiluted human saliva. For example, the resulting calibration plot in inset of FIG. 13A exhibited good sensitivity and linearity. Salivary uric acid level was estimated in the normal range in human saliva without any stimulation. Although, due to interferents like proteins in saliva, sensitivity in real saliva was slightly decreased compared to it in artificial saliva, yet the current response was well-defined and distinguishable to physiological level of uric acid. Furthermore, stability was evaluated in human saliva to confirm anti-biofouling from saliva proteins, as shown in FIG. 13B, in which the exemplary results indicated that the present uric acid biosensor can be expanded to use of monitoring treatment of acute gout, for example. For example, acute gout should include real time monitoring and fast treatment, which can be addressed by the exemplary PB-PPD-Uricase biosensor. Notably, salivary uric acid level shows faster response to medication than its level in blood. The exemplary mouthguard salivary uric acid biosensor shows good linear response and stable response in undiluted human saliva and this implies practical clinical use for hyperuricemia patient.

The exemplary implementations of the PB-PPD-Uricase biosensor included monitoring salivary uric acid levels of a hyperuricemia patient under medication treatment. Salivary uric acid level was compared by the developed mouthguard biosensor between a healthy person and a hyperuricemia patient (already diagnosed from medical doctor). To verify fluctuation of salivary uric acid level during the day, saliva was collected and measured from each subject (normal person and hyperuricemia patient) without any treatment to saliva sample at every hour for 5 hours. Each sample was measured by standard addition method to know the amount of uric acid in saliva sample.

Normal salivary uric acid level is considered to be between 250 μM and 350 μM, and a person who has higher than 350 μM can be considered as hyperuricemia. To check practical use in clinic, salivary uric acid level was measured and compared from normal person and patient who is already diagnosed as hyperuricemia from medical doctor. When hyperuricemia patient has higher salivary uric acid level than normal level, Allopurinol® medication was taken for 4 days in a row following medication and daily salivary uric acid level was measured to confirm treatment effect of medication (e.g., Allopurinol®). Allopurinol® is a medication that inhibits a xanthine oxidase, which can treat hyperuricemia and its related symptoms, including gout. For these exemplary implementations, saliva was collected every day, three times per day, and the standard addition method was performed.

Figure 14A:
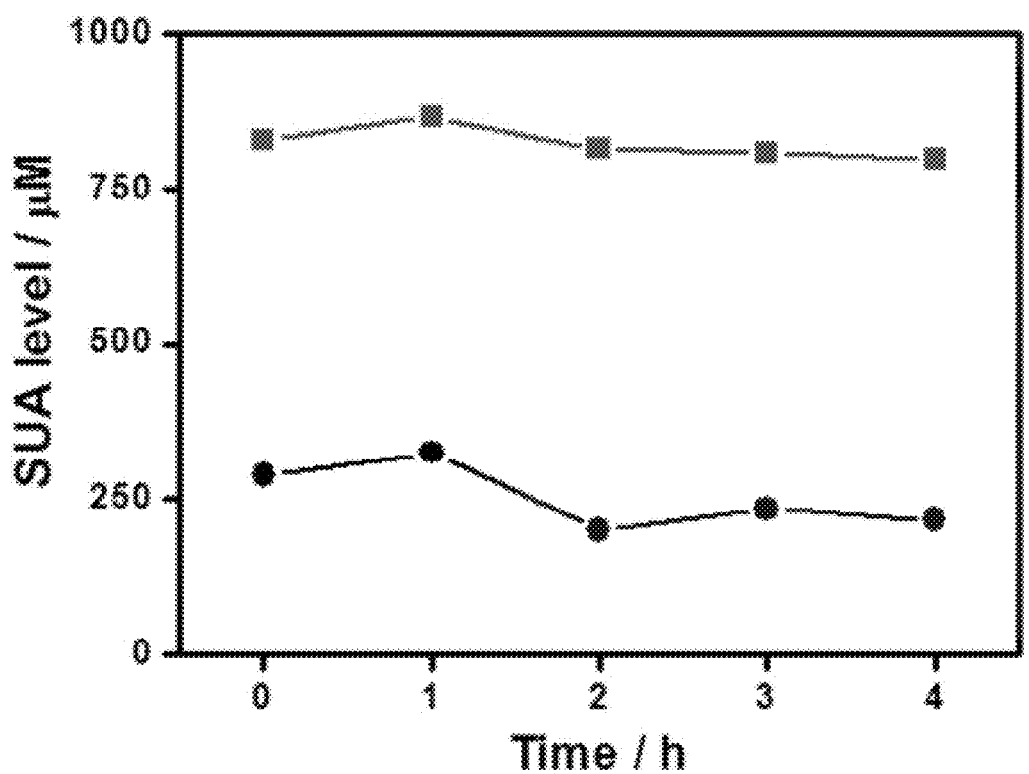
FIG. 14A shows a data plot of salivary uric acid levels obtained by continuous monitoring using an exemplary biosensor of a healthy person and a hyperuricemia patient.
Figure 14B:
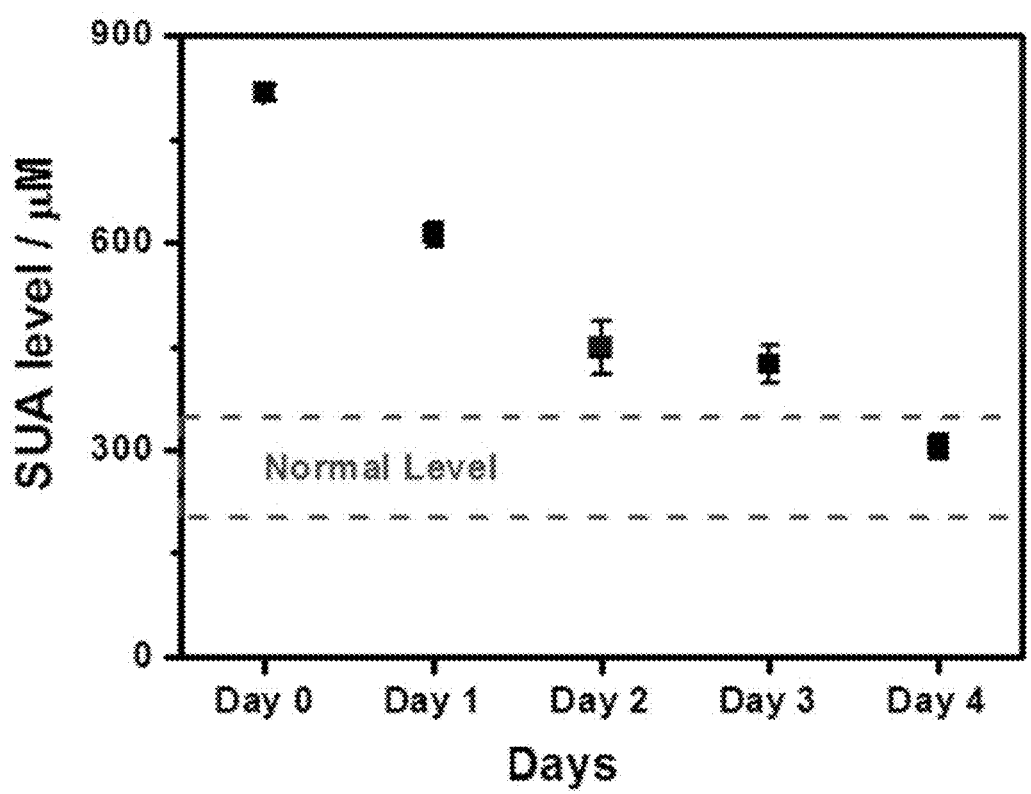
FIG. 14B shows a data plot of salivary uric acid levels of the hyperuricemia patient monitored by the exemplary biosensor for multiple days while under treatment.

FIG. 14A shows a data plot of salivary uric acid levels obtained by continuous monitoring using the exemplary biosensor for 5 hours of a normal person ('●', black circles) and a hyperuricemia patient ('■', red squares). FIG. 14B shows a data plot of salivary uric acid levels of the hyperuricemia patient monitored using the exemplary biosensor over 5 days while under treatment for hyperuricemia with Alopurinol®. The exemplary result is obtained by average of three times of measurement.

As shown in the data plot of FIG. 14A, stable salivary uric acid value were continuously monitored using the exemplary PB-PPD-Uricase biosensor. The exemplary results indicated the salivary uric acid levels do not fluctuates depending on time regardless of normal person or patient. Also, high and reproducible uric acid value in saliva from patient demonstrated the feasibility of the exemplary mouthguard sensor as a diagnostic tool for hyperuricemia.

Allopurinol medication is used to bring the uric acid level back to normal range. It is noted that this medication was used for controlling uric acid levels of the hyperuricemia patient. As shown in FIG. 14B, a high level of salivary uric acid at the first day (i.e., day 0) was confirmed, and subject started to take Allopurinol medication 4 days in a row. After taking 4 days of the medication, the salivary uric acid level returned back to a normal level, all of which monitored by the exemplary PB-PPD-Uricase biosensor.

Other biochemicals present in saliva can also be detected and utilized to extract energy by the disclosed mouth-based biosensor and biofuel cell device platform. In one example, cortisol can be electrochemically detected (e.g., in a range of 0.05 μg/dL to 0.5 μg/dL) using the disclosed salivary biosensor, from which the data can be used to indicate or determine physical or psychological stress markers or disorders, e.g., such as Cushing's Syndrome. In one exemplary embodiment of a salivary cortisol biosensor, the modified electrode structure 102a of the biosensor 100 can include a layer (e.g., layer 107) including antibodies of cortisol (e.g., Cortisol Ag-Ab/AP) entrapped to the electrode 106.

In another example, alpha-amylase can be electrochemically detected (e.g., in a range of 10 U/mL to 250 U/mL) using the disclosed salivary biosensor, from which the data can be used to indicate or determine physical or psychological stress markers or disorders. In one exemplary embodiment of a salivary alpha-amylase biosensor, the modified electrode structure 102a of the biosensor 100 can include a layer (e.g., layer 107) including glucose oxidase (GOx) with glucosidase (GD) entrapped to the electrode 106.

In another example, salivary phosphate can be electrochemically detected (e.g., in a micromolar range) using the disclosed salivary biosensor, from which the data can be used to indicate various conditions, e.g., such as hyperphosphatemia, or ovulation, or be used in the course of dental care. In one exemplary embodiment of a salivary phosphate biosensor, the modified electrode structure 102a of the biosensor 100 can include a layer (e.g., layer 107) including lactate oxidase (LOx) or pyruvate oxidase (PyOx) entrapped to the electrode 106 (e.g. Prussian Blue carbon).

In another example, cadmium can be electrochemically detected (e.g., at levels up to 100 μg/L or greater) using the disclosed salivary biosensor, from which the data can be used for various applications, e.g., such as biomonitoring of environmental factors present in a user's environment or of smoking. In another example, salivary fluoride or calcium can be electrochemically detected (e.g., in a range of 0.05 ppm to 0.01 ppm, or even in ranges less than 0.01 ppm) using the disclosed salivary biosensor, from which the data can be used to in dental care (e.g., such as identify the presence of cavities). In another example, pH levels can be detected using the disclosed salivary biosensor, from which the data can be used to indicate various conditions related to oral health or to determine the presence of stress markers.

EXAMPLES

The following examples are illustrative of several embodiments of the present technology. Other exemplary embodiments of the present technology may be presented prior to the following listed examples, or after the following listed examples.

In an example of the present technology (example 1), an electrochemical sensor device for detecting analytes in saliva includes a substrate including an electrically insulative material; a first electrode disposed on the substrate at a first location, in which the first electrode includes a surface including a chemical substance that includes a catalyst or a reactant corresponding to an analyte in saliva; and a second electrode disposed on the substrate at a second location separated from the first electrode by a spacing region, the first and second electrodes capable of sustaining a redox reaction including the chemical substance and analyte to produce an electrical signal, such that, when the device is present in the mouth of a user and electrically coupled to an electrical circuit, the device is operable to detect the analyte in the user's saliva.

Example 2 includes the device as in example 1, in which the surface of the first electrode is structured to include the chemical substance immobilized on the first electrode surface by electropolymeric entrapment in a polymer film or selectively permeable scaffold.

Example 3 includes the device as in example 2, in which the polymer film includes poly(o-phenylenediamine).

Example 4 includes the device as in example 2, in which the selectively permeable scaffold includes Nafion or chitosan.

Example 5 includes the device as in example 1, in which the surface of the first electrode is structured to include the chemical substance dispersed within a material forming the first electrode.

Example 6 includes the device as in example 1, in which the surface of the first electrode is structured to include a layer containing the chemical substance attached to the surface electrostatically or covalently.

Example 7 includes the device as in example 1, in which the chemical substance includes lactate oxidase (LOx), and the analyte for detection by the device includes lactate.

Example 8 includes the device as in example 1, in which the chemical substance includes glucose oxidase (GOx), and the analyte for detection by the device includes glucose.

Example 9 includes the device as in example 1, in which the chemical substance includes uric acid oxidase (uricase), and the analyte for detection by the device includes uric acid.

Example 10 includes the device as in example 1, in which the first electrode, the second electrode, or both include an electrically conductive material including an electrocatalyst.

Example 11 includes the device as in example 10, in which the first electrode, the second electrode, or both include an electrically conductive including Prussian-Blue Carbon.

Example 12 includes the device as in example 1, in which the substrate is included in a mouthguard conformed to fit within the mouth of the user, in which the first and second locations of the first and second electrodes are positioned on an interior region of the mouthguard proximate to the user's tongue.

Example 13 includes the device as in example 1, further including a first electrode interface component disposed on the substrate and electrically coupled to the first electrode via a first conduit that is electrically conductive; and a second electrode interface component disposed on the substrate and electrically coupled to the second electrode via a second conduit that is electrically conductive, in which the first and second electrode interface components are electrically coupled to the electrical circuit.

Example 14 includes the device as in example 1, in which the first electrode is operable as a working electrode and the second electrode is operable as a counter electrode for amperometry measurements, and the device further includes a reference electrode positioned between the working and counter electrodes on the substrate and having a surface including the chemical substance.

Example 15 includes the device as in example 1, further including a biofuel cell disposed on the substrate to electrochemically extract energy from the saliva to provide power to the device, in which the biofuel cell includes an anode disposed on the substrate and including an electrically conductive material, the anode including a fuel cell catalyst to facilitate the conversion of a fuel substance in the saliva to a first product in an oxidative process that releases electrons captured at the anode, thereby extracting energy from the fuel substance, and a cathode disposed on the substrate adjacent to and separated from the anode, the cathode including a material that is electrically conductive and capable of reducing an oxygenated substance in the saliva to a second product in a chemical reduction process in which the second product gains electrons; and the electrical circuit electrically coupled between the biofuel cell and the first and second electrodes, via electrical interconnects, to obtain the extracted energy as electrical energy from the biofuel cell and to supply the electrical energy to the first and second electrodes of the device.

Example 16 includes the device as in example 15, in which fuel cell catalyst is encased on the surface of the anode in a porous scaffold structure formed of a conducting polymer.

Example 17 includes the device as in example 17, in which the conducting polymer includes at least one of polyaniline, polypyrrole, polythiophene, poly(3,4-ethylenedioxythiophene), poly(p-phenylene sulfide), polyfluorine, polyphenylene, polypyrene, polyazulene, polynaphthalene, poly(acetylene), poly(p-phenylene vinylene), or polyphenyldiamine.

Example 18 includes the device as in example 15, in which the fuel cell catalyst is entrapped in a selectively permeable membrane coupled to the surface of the anode.

Example 19 includes the device as in example 18, in which the permeable-selective membrane includes at least one of Nafion or chitosan.

Example 20 includes the device as in example 15, in which the fuel cell catalyst is electrostatically or covalently bound to the surface of the anode.

Example 21 includes the device as in example 15, in which the anode is structured to include an electroactive mediator to facilitate electron transfer between an active site of the fuel cell catalyst and the surface of the anode.

Example 22 includes the device as in example 15, in which the fuel cell catalyst includes LOx, GOx, or uricase.

Example 23 includes the device as in example 15, in which the cathode includes an electroactive mediator capable of reducing a non-oxygenated substance in the saliva to the second product in the chemical reduction process in which the second product gains electrons.

Example 24 includes the device as in example 15, in which the electrical circuit includes a signal conditioning circuit to modify the electrical energy extracted by the biofuel cell, or to amplify the detected electrical signal by the first and second electrodes, or both.

Example 25 includes the device as in example 15, in which the electrical circuit includes a data processing unit including a processor to process data based on the detected electrical signal and a memory to store or buffer the data.

In an example of the present technology (example 26), a method to detect an analyte in saliva and power a device from the saliva includes extracting electrical energy, at anode and cathode electrodes of a biofuel cell attached to a mouth-based device wearable in the mouth of a user, from a biofuel substance present in saliva by converting the biofuel substance to a first product in an oxidative process that releases electrons captured at the anode and reducing a chemical substance in the saliva to a second product in a chemical reduction process in which the second product gains electrons at the cathode; supplying the extracted electrical energy to electrodes of an electrochemical sensor attached to the mouth-based device to activate the electrochemical sensor; and detecting, at the electrodes of the activated electrochemical sensor in contact with saliva in the user's mouth, an electrical signal produced as a result of a redox reaction involving an analyte in the saliva and a chemical agent coupled to an electrode of the electrochemical sensor.

Example 27 includes the method as in example 26, in which the electrical signal is detected using amperometry, voltammetry, or potentiometry.

Example 28 includes the method as in example 26, further including processing the electrical signal to determine a parameter of the analyte.

Example 29 includes the method as in example 28, in which the parameter includes a concentration level of the analyte.

Example 30 includes the method as in example 26, further including wirelessly transmitting the detected electrical signal to an external device.

In an example of the present technology (example 31), a device to detect an analyte in saliva and power a device from the saliva includes a substrate including an electrically insulative material, in which the substrate is structured to attach to a mouth-worn device that can fit inside a mouth of a user; an electrochemical sensor to detect a salivary analyte; a biofuel cell to electrochemically extract energy from the saliva to provide electrical power to the device, and an electrical circuit electrically coupled between the biofuel cell and the electrochemical sensor via electrical interconnects to obtain the extracted energy as electrical energy from the biofuel cell and to supply the electrical energy to the electrochemical sensor. The electrochemical sensor includes a first electrode disposed on the substrate at a first location, in which the first electrode includes a surface including a chemical substance that includes a catalyst or a reactant corresponding to the salivary analyte; and a second electrode disposed on the substrate at a second location separated from the first electrode by a spacing, in which the first and second electrodes are operable to sustain a redox reaction involving the chemical substance and the salivary analyte to produce an electrical signal detectable by the first and second electrodes. The biofuel cell includes an anode disposed on the substrate and including an electrically conductive material, the anode including a fuel cell catalyst to facilitate the conversion of a fuel substance in the saliva to a first product in an oxidative process that releases electrons captured at the anode, thereby extracting energy from the fuel substance, and a cathode disposed on the substrate adjacent to and separated from the anode, the cathode including a material that is electrically conductive and capable of reducing an oxygenated substance in the saliva to a second product in a chemical reduction process in which the second product gains electrons. When the device is present in the mouth of the user, the device is operable to detect the salivary analyte in the user's saliva.

Example 32 includes the device as in example 31, in which the electrical circuit includes a signal conditioning circuit to modify the electrical energy extracted by the biofuel cell, or to amplify the detected electrical signal by the first and second electrodes, or both.

Example 33 includes the device as in example 31, in which the electrical circuit includes a data processing unit a processor to process data based on the detected electrical signal and a memory to store or buffer the data.

Example 34 includes the device as in example 31, in which the electrical circuit includes a wireless communications unit to wirelessly transmit the detected electrical signal to an external device.

Example 35 includes the device as in example 31, in which the surface of the first electrode is structured to include the chemical substance immobilized on the first electrode surface by electropolymeric entrapment in a polymer film or selectively permeable scaffold; or the chemical substance dispersed within a material forming the first electrode; or a layer containing the chemical substance attached to the surface electrostatically or covalently.

Example 36 includes the device as in example 35, in which the polymer film includes poly(o-phenylenediamine), or in which the selectively permeable scaffold includes Nafion or chitosan.

Example 37 includes the device as in example 31, in which the electrochemical sensor is configured by one or more of the following: the chemical substance includes lactate oxidase (LOx), and the analyte for detection by the electrochemical sensor includes lactate; the chemical substance includes glucose oxidase (GOx), and the analyte for detection by the electrochemical sensor includes glucose; the chemical substance includes uric acid oxidase (uricase), and the analyte for detection by the electrochemical sensor includes uric acid; the chemical substance includes an antibody of cortisol, and the analyte for detection by the electrochemical sensor includes cortisol; the chemical substance includes GOx and glucosidase (GD), and the analyte for detection by the electrochemical sensor includes alpha-amylase; and/or the chemical substance includes LOx or pyruvate oxidase (PyOx), and the analyte for detection by the electrochemical sensor includes phosphate.

Example 38 includes the device as in example 31, in which the substrate is included in a mouthguard conformed to fit within the mouth of the user, in which the first and second locations of the first and second electrodes are positioned on an interior region of the mouthguard proximate to the user's tongue.

Example 39 includes the device as in example 31, in which the first electrode is operable as a working electrode and the second electrode is operable as a counter electrode for amperometry measurements, and the electrochemical sensor further includes a reference electrode positioned between the working and counter electrodes on the substrate and having a surface including the chemical substance.

Example 40 includes the device as in example 31, in which fuel cell catalyst is encased on the surface of the anode in a porous scaffold structure formed of a conducting polymer; or the fuel cell catalyst is entrapped in a selectively permeable membrane coupled to the surface of the anode; or the fuel cell catalyst is electrostatically or covalently bound to the surface of the anode.

Example 41 includes the device as in example 40, in which the conducting polymer includes at least one of polyaniline, polypyrrole, polythiophene, poly(3,4-ethylenedioxythiophene), poly(p-phenylene sulfide), polyfluorine, polyphenylene, polypyrene, polyazulene, polynaphthalene, poly(acetylene), poly(p-phenylene vinylene), or polyphenyldiamine.

Example 42 includes the device as in example 40, in which the permeable-selective membrane includes at least one of Nafion or chitosan.

Example 43 includes the device as in example 31, in which the anode is structured to include an electroactive mediator to facilitate electron transfer between an active site of the fuel cell catalyst and the surface of the anode.

Example 44 includes the device as in example 31, in which the fuel cell catalyst includes LOx, GOx, or uricase.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A biofuel cell device for powering a mouth apparatus, comprising:
    a substrate including an electrically insulative material and configured in a mouth-worn device that can fit inside a mouth of a user, wherein the mouth-worn device includes an electronic device and
    a biofuel cell to electrochemically extract energy from saliva to provide electrical power to the electronic device, the biofuel cell comprising:
        an anode disposed on the substrate and including an electrically conductive material, the anode including a fuel cell catalyst to facilitate a conversion of a fuel substance in the saliva to a first product in an oxidative process that releases electrons captured at the anode, thereby extracting energy from the fuel substance, and
        a cathode disposed on the substrate adjacent to and separated from the anode, the cathode including a material that is electrically conductive and capable of reducing an oxygenated substance in the saliva to a second product in a chemical reduction process in which the second product gains electrons,
        wherein the biofuel cell is electrically coupled to the electronic device via electrical interconnects to supply the extracted energy as electrical energy to the electronic device,
    wherein the mouth-worn device includes a mouthguard,
    wherein the electronic device includes a biosensor comprising an electrochemical sensor operable to detect an analyte in the saliva when the mouthguard is present in the mouth of the user, the electrochemical sensor including a first electrode and a second electrode, wherein the first and second electrodes are positioned on an external surface of an interior region of a side of the mouthguard to interface the saliva continuously, wherein the interior region of the mouthguard defines a space between sections of the mouthguard proximate to and sized to accommodate the user's tongue when the mouthguard is positioned in the user's mouth.

2. The biofuel cell device as in claim 1, wherein fuel cell catalyst is encased on a surface of the anode in a porous scaffold structure formed of a conducting polymer.

3. The biofuel cell device as in claim 2, wherein the conducting polymer includes at least one of polyaniline, polypyrrole, polythiophene, poly(3,4-ethylenedioxythiophene), poly(p-phenylene sulfide), polyfluorine, polyphenylene, polypyrene, polyazulene, polynaphthalene, poly(acetylene), poly(p-phenylene vinylene), or polyphenyldiamine.

4. The biofuel cell device as in claim 1, wherein the fuel cell catalyst is entrapped in a permeable-selective membrane coupled to a surface of the anode.

5. The biofuel cell device as in claim 4, wherein the permeable-selective membrane includes at least one of Nafion or chitosan.

6. The biofuel cell device as in claim 1, wherein the fuel cell catalyst is electrostatically or covalently bound to a surface of the anode.

7. The biofuel cell device as in claim 1, wherein the anode is structured to include an electroactive mediator to facilitate electron transfer between an active site of the fuel cell catalyst and a surface of the anode.

8. The biofuel cell device as in claim 1, wherein the fuel cell catalyst includes lactate oxidase (LOx), glucose oxidase (GOx), or uricase.

9. The biofuel cell device as in claim 1, wherein the cathode includes an electroactive mediator capable of reducing a non-oxygenated substance in the saliva to the second product in the chemical reduction process in which the second product gains electrons.

10. The biofuel cell device as in claim 1, wherein the electronic device includes a signal conditioning circuit to modify the electrical energy extracted by the biofuel cell.

11. The biofuel cell device as in claim 1, wherein the biosensor includes a pH sensor.

12. The biofuel cell device as in claim 1, wherein the first electrode is disposed on the substrate at a first location, wherein the first electrode includes a surface including a chemical substance that includes a catalyst or a reactant corresponding to the analyte in the saliva; and the second electrode is disposed on the substrate at a second location separated from the first electrode by a spacing region, the first and second electrodes capable of sustaining a redox reaction including the chemical substance and the analyte to produce an electrical signal.

13. The biofuel cell device as in claim 12, wherein the electronic device includes a data processing unit including a processor to process data based on the electrical signal and a memory to store or buffer the data.

14. The biofuel cell device as in claim 12, wherein the first electrode includes a first bar portion and the second electrode includes a second bar portion that are spaced apart on the side of the mouthguard.

15. The biofuel cell device as in claim 12, wherein the first electrode, the second electrode, or both include an electrically conductive material comprising Prussian-Blue Carbon.

16. A method for powering a mouth-worn device from saliva, comprising:
(a) providing a biofuel cell device for the mouth-worn device that includes a mouthguard that can fit inside a mouth of a user and that includes an electronic device, wherein the biofuel cell device comprises (i) a substrate including an electrically insulative material, and (ii) a biofuel cell to electrochemically extract energy from saliva to provide electrical power to the electronic device, wherein the biofuel cell comprises (1) an anode disposed on the substrate and including an electrically conductive material, the anode including a fuel cell catalyst to facilitate a conversion of a biofuel substance in the saliva to a first product in an oxidative process that releases electrons captured at the anode, thereby extracting energy from the biofuel substance, and (2) a cathode disposed on the substrate adjacent to and separated from the anode, the cathode including a material that is electrically conductive and capable of reducing an oxygenated substance in the saliva to a second product in a chemical reduction process in which the second product gains electrons,
wherein the biofuel cell is electrically coupled to the electronic device via electrical interconnects to supply the extracted energy to the electronic device, and
wherein the electronic device includes a biosensor comprising an electrochemical sensor operable to detect an analyte in the saliva when the mouthguard is present in the mouth of the user, the electrochemical sensor including a first electrode and a second electrode, wherein the first and second electrodes are positioned on an external surface of an interior region of a side of the mouthguard to interface the saliva continuously, and wherein the interior region of the mouthguard defines a space between sections of the mouthguard proximate to and sized to accommodate the user's tongue when the mouthguard is positioned in the user's mouth;
(b) extracting electrical energy, at the anode and the cathode of the biofuel cell when the mouth-worn device is worn inside the mouth of the user, from the biofuel substance present in the saliva; and
(c) supplying the extracted electrical energy to the electronic device to provide power to the electrochemical sensor.

17. The method as in claim 16, further comprising:
detecting, at the first and second electrodes of the electrochemical sensor in contact with the saliva in the user's mouth, an electrical signal produced as a result of a redox reaction involving the analyte in the saliva and a chemical agent coupled to an electrode of the electrochemical sensor.

18. The method as in claim 17, further comprising:
processing the electrical signal to determine a parameter of the analyte.

19. A biofuel cell device adapted for powering an apparatus in a person's mouth, comprising:
a substrate including an electrically insulative material and configured in a mouth-worn device that can fit inside a mouth of a user, wherein the mouth-worn device includes an electronic device comprising an electrical circuit; and
a biofuel cell to electrochemically extract energy from saliva to provide electrical power to the electronic device, the biofuel cell comprising:
an anode disposed on the substrate and including an electrically conductive material, the anode including a fuel cell catalyst to facilitate a conversion of a fuel substance in the saliva to a first product in an oxidative process that releases electrons captured at the anode, thereby extracting energy from the fuel substance, and
a cathode disposed on the substrate adjacent to and separated from the anode, the cathode including a material that is electrically conductive and capable of reducing an oxygenated substance in the saliva to a second product in a chemical reduction process in which the second product gains electrons,
wherein the biofuel cell is electrically coupled to the electrical circuit of the electronic device via electrical interconnects to supply the extracted energy as electrical energy to the electronic device,
wherein the mouth-worn device includes a mouthguard, and wherein the electronic device includes a biosensor,
wherein, when the mouthguard is present in the mouth of the user, the biosensor is operable to detect an analyte in the user's saliva, wherein the biosensor includes an electrochemical sensor, the electrochemical sensor comprising:
   a first electrode disposed on the substrate at a first location, wherein the first electrode includes a surface including a chemical substance that includes a catalyst or a reactant corresponding to the analyte in the saliva; and
   a second electrode disposed on the substrate at a second location separated from the first electrode by a spacing region, the first and second electrodes capable of sustaining a redox reaction including the chemical substance and the analyte to produce an electrical signal,
wherein, when the mouth-worn device is present in the mouth of the user and the electrochemical sensor is electrically coupled to the electrical circuit, the electrochemical sensor is operable to detect the analyte in the user's saliva,
wherein the first electrode includes a first bar portion and the second electrode includes a second bar portion that are spaced apart on a side of the mouthguard, and
wherein the first and second locations of the first and second electrodes are positioned on an external surface of an interior region of the side of the mouthguard to interface the saliva continuously, wherein the interior region of the mouthguard defines a space between sections of the mouthguard proximate to and sized to accommodate the user's tongue when the mouthguard is positioned in the user's mouth.

20. The biofuel cell device as in claim 19, wherein the biosensor includes a pH sensor.

* * * * *